United States Patent [19]

Davidson et al.

[11] Patent Number: 5,514,677
[45] Date of Patent: May 7, 1996

[54] HYDROXAMIC ACID BASED COLLAGENASE INHIBITORS

[75] Inventors: Alan H. Davidson, Witney; Jonathan P. Dickens, High Wycombe; Michael J. Crimmin, Ascot, all of England

[73] Assignee: British Biotech Pharmaceuticals Limited, Oxford, England

[21] Appl. No.: 229,154

[22] Filed: Apr. 18, 1994

Related U.S. Application Data

[62] Division of Ser. No. 674,363, filed as PCT/GB89/01398, Nov. 23, 1989, Pat. No. 5,304,604.

[30] Foreign Application Priority Data

Nov. 23, 1988 [GB] United Kingdom ................... 8827308

[51] Int. Cl.$^6$ .................... C07C 259/06; A61K 31/13
[52] U.S. Cl. .................. 514/238.2; 514/317; 514/357; 514/394; 514/400; 514/427; 514/428; 514/616; 544/168; 548/309.7; 548/338.1; 548/561; 548/571; 564/153; 546/233; 546/337
[58] Field of Search .................. 564/153; 548/309.7, 548/338.1, 561, 571; 544/160; 546/233, 337; 514/238.2, 317, 357, 394, 400, 427, 428, 610

[56] References Cited

U.S. PATENT DOCUMENTS

| | | |
|---|---|---|
| 4,105,789 | 8/1978 | Ondetti et al. . |
| 4,496,540 | 1/1985 | Kim . |
| 4,599,361 | 7/1986 | Dickens et al. . |
| 4,738,803 | 4/1988 | Roques . |
| 5,304,604 | 4/1984 | Davidson . |

FOREIGN PATENT DOCUMENTS

| | | |
|---|---|---|
| 0214639 | 3/1987 | European Pat. Off. . |
| 0236872 | 9/1987 | European Pat. Off. . |
| 0274453 | 7/1988 | European Pat. Off. . |
| 0012401 | 6/1989 | European Pat. Off. . |

OTHER PUBLICATIONS

Woolley et al, Collagenase at Sites of Cartilage Erosion in the Rheumatoid Joint, *Arthritis and Rheumatism*, vol. 20, No. 6, 1231–1239 (1977).
Cawston et al., A Rapid and Reproducible Assay for Collagenase Using [1–$^{14}$C]Acetylated Collagen, *Analytical Biochemistry*, vol. 99, 340–345 (1979).
Cawston et al, Purification of rabbit bone inhibitor of collagenase, *Biochem. J.*, vol. 195, 159–165 (1981).
Cawston et al, Mammalian Collagenases, *Methods in Enzymology*, vol. 80, 781 (1981).
Hayward et al, *The Effect of Reversal of the Direction of Peptide Bonds on the Interaction Between Peptide Hormones and Receptors*, Pept. Proc. Eur. Pept. Symp. 13th, 287–298 (1974, published 1975).
Amomoto et al, Microbiol. Immunol. 28 85 (1984) Abstact Only.

*Primary Examiner*—Robert Gerstl
*Attorney, Agent, or Firm*—Banner & Allegretti, Ltd.

[57] ABSTRACT

Compounds of general formula I:

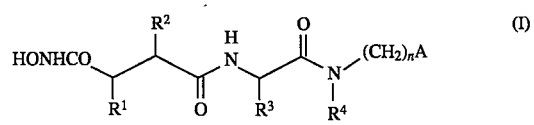

wherein:

A represents the group —NH$_2$, a substituted acyclic amine or a heterocyclic base;

have collagenase inhibition activity and are useful in the management of disease involving tissue degradation and/or the promotion of wound healing. Diseases involving tissue degradation include arthropathy (particularly rheumatoid arthritis), inflammation, dermatological diseases, bone resorption diseases and tumour invasion.

8 Claims, No Drawings

HYDROXAMIC ACID BASED COLLAGENASE INHIBITORS

This is a divisional of application Ser. No. 07/674,363, filed as PCT/GB89/01398, Nov. 23, 1989 and issued as U.S. Pat. No. 5,304,604 on Apr. 19, 1994.

This invention relates to pharmaceutically and veterinarily active compounds, which are derivatives of hydroxamic acid.

The compounds of the present invention act as inhibitors of metalloproteases involved in tissue degradation, such as collagenase, which initiates collagen breakdown, stromelysin (protoglycanase), gelatinase and collagenase (IV). There is evidence implicating collagenase as one of the key enzymes in the breakdown of articular cartilage and bone in rheumatoid arthritis (*Arthritis and Rheumatism*, 20, 1231–1239, 1977). Potent inhibitors of collagenase and other metalloproteases involved in tissue degradation are useful in the treatment of rheumatoid arthritis and related diseases in which collagenolytic activity is important. Inhibitors of metalloproteases of this type can therefore be used in treating or preventing conditions which involve tissue breakdown; they are therefore useful in the treatment of arthropathy, dermatological conditions, bone resorption, inflammatory diseases and tumour invasion and in the promotion of wound healing. Specifically, compounds of the present invention may be useful in the treatment of osteopenias such as osteoporosis, rheumatoid arthritis, osteoarthritis, periodontitis, gingivitis, corneal ulceration and tumour invasion.

A number of small peptide like compounds which inhibit metalloproteases have been described. Perhaps the most notable of these are those relating to the angiotensin converting enzyme (ACE) where such agents act to block the conversion of the decapeptide angiotensin I to angiotensin II a potent pressor substance. Compounds of this type are described in EP-A-0012401.

Certain hydroxamic acids have been suggested as collagenase inhibitors as in U.S. Pat. No. 4,599,361 and EP-A-0236872. Other hydroxamic acids have been prepared as ACE inhibitors, for example in U.S. Pat. No. 4,105,789, while still others have been described as enkephalinase inhibitors as in U.S. Pat. No. 4,496,540.

EP-A-0012401 discloses antihypertensive compounds of the formula:

$$\underset{R^2}{\overset{O}{\underset{\|}{R-C}}}-\underset{}{\overset{R^1}{\underset{|}{C}}}-NH-CH-\underset{\underset{O}{\overset{\|}{C}}}{\overset{R^3}{\underset{|}{C}}}-\underset{R^7}{\overset{R^4}{\underset{|}{N}}}-\underset{}{\overset{R^5}{\underset{|}{C}}}-R^6$$

wherein

R and $R^6$ are the same or different and are hydroxy, alkoxy, alkenoxy, dialkylamino alkoxy, acylamino alkoxy, acyloxy alkoxy, aryloxy, alkyloxy, substituted aryloxy or substituted aralkoxy wherein the substituent is methyl, halo, or methoxy, amino, alkylamino, dialkylamino, aralkylamino or hydroxyamino;

$R^1$ is hydrogen, alkyl of from 1 to 20 carbon atoms, including branched cyclic and unsaturated alkyl groups;

substituted alkyl wherein the substituent is halo, hydroxy, alkoxy, aryloxy amino, alkylamino, dialkylamino, acrylamino, arylamino, guanidino, imidazolyl, indolyl, mercapto, alkylthio, arylthio, carboxy, carboxamido, carbalkoxy, phenyl, substituted phenyl wherein the substituent is alkyl, alkoxy or halo; aralkyl or heteroaralkyl, aralkenyl or heteroaralkenyl, substituted aralkyl, substituted heteroaralkyl, substituted aralkenyl or substituted hetereoaralkenyl, wherein the substituent is halor or dihalo, alkyl, hydroxy, alkoxy, amino, aminomethyl, acrylamino, dialkylamino, alkylamino, carboxyl, haloalkyl, cyano or sulphonamido, aralkyl or hetereoaralkyl substituted on the alkyl portion by amino or acylamino;

$R^2$ and $R^7$ are hydrogen or alkyl;

$R^3$ is hydrogen, alkyl, phenylalkyl, aminomethylphenylalkyl, hydroxyphenylalkyl, hydroxyalkyl, acetylaminoalkyl, acylaminoalkyl, acylaminoalkyl aminoalkyl, dimethylaminoalkyl, haloalkyl, guanidinoalkyl, imidazolylalkyl, indolylalkyl, mercaptoalkyl and alkylthioalkyl;

$R^4$ is hydrogen or alkyl;

$R^5$ is hydrogen, alkyl, phenyl, phenylalkyl, hydroxyphenylalkyl, hydroxyalkyl, aminoalkyl, guanidinoalkyl, imidazolylalkyl, indolylalkyl, mercaptoalkyl or alkylthioalkyl;

$R^4$ and $R^5$ may be connected together to form an alkylene bridge of from 2 to 4 carbon atoms, an alkylene bridge of from 2 to 3 carbon atoms and one sulphur atom, an alkylene bridge of from 3 to 4 carbon atoms containing a double bond or an alkylene bridge as above, substituted with hydroxy, alkoxy or alkyl and the pharmaceutically acceptable salts thereof.

U.S. Pat. No. 4,599,361 discloses compounds of the formula:

$$\underset{}{\overset{O}{\underset{\|}{HOHNC}}}-A-\underset{}{\overset{O}{\underset{\|}{CNH}}}-\underset{\underset{a}{}}{\overset{R^2}{\underset{|}{CH}}}-\underset{}{\overset{O}{\underset{\|}{CNHR^1}}}$$

wherein $R^1$ is $C_1$–$C_6$ alkyl;

$R^2$ is $C_1$–$C_6$ alkyl, benzyl, benzyloxybenzyl, ($C_1$–$C_6$ alkoxy)benzyl or benzyloxy($C_1$–$C_6$ alkyl);

a is a chiral centre with optional R or S stereochemistry;

A is a $$-(\underset{b}{\overset{}{CHR^3}}-\underset{c}{\overset{}{CHR^4}})-\text{group}$$

or a —($CR^3$=$CR^4$)— group wherein b and c are chiral centres with optional R or S stereochemistry;

$R^3$ is hydrogen, $C_1$–$C_6$ alkyl, phenyl or phenyl($C_1$–$C_6$ alkyl) and $R^4$ is hydrogen, $C_1$–$C_6$ alkyl, phenyl($C_1$–$C_6$ alkyl), cycloalkyl or cycloalkyl($C_1$–$C_6$ alkyl).

EP-A-0236872 discloses generically compounds of the formula $$\underset{R^3}{\overset{A}{\underset{|}{HC}}}-\underset{}{\overset{R^1}{\underset{|}{CH}}}-CO-NH-\underset{}{\overset{R^2}{\underset{|}{CH}}}-CO-\underset{R^6}{\overset{R^4}{\underset{|}{N}}}-CH-R^5$$

wherein

A represents a group of the formula HN(OH)—CO— or HCO—N(OH)—;

$R^1$ represents a $C_2$–$C_5$ alkyl group;

$R^2$ represents the characterising group of a natural alpha-amino acid in which the functional group can be protected, amino groups may be acylated and carboxyl groups can be amidated, with the proviso that $R^2$ can not represent hydrogen or a methyl group;

R³ represents hydrogen or an amino, hydroxy, mercapto, $C_1-C_6$ alkyl, $C_1-C_6$ alkoxy, $C_1-C_6$ acylamino, $C_1-C_6$-alkylthio, aryl-($C_1-C_6$ alkyl)-, amino-($C_1-C_6$-alkyl)-, hydroxy($C_1-C_6$-alkyl)-, mercapto($C_1-C_6$ alkyl) or carboxy($C_1-C_6$ alkyl) group, wherein the amino, hydroxy, mercapto or carboxyl groups can be protected and the amino groups may be acylated or the carboxyl groups may be amidated;

R⁴ represents hydrogen or a methyl group;

R⁵ represents hydrogen or a $C_1-C_6$ acyl, $C_1-C_6$ alkoxy-$C_1-C_6$ alkyl, di($C_1-C_6$-alkoxy)methylene, carboxy, ($C_1-C_6$ alkyl)carbinyl, ($C_1-C_6$ alkoxy)carbinyl, arylmethoxy carbinyl, ($C_1-C_6$ alkyl)amino carbinyl or arylamino carbinyl group; and R⁶ represents hydroxy or a methylene group; or R² and R⁴ together represent a group $—(CH_2)_n—$, wherein n represents a number from 4 to 11; or R⁴ and R⁵ together represent a trimethylene group;

and pharmaceutically acceptable salts of such compounds, which are acid or basic.

U.S. Pat. No. 4,105,789 generically discloses compounds which have the general formula

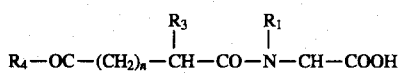

and salts thereof, wherein

R₁ is hydrogen, lower alkyl, phenyl lower alkylene, hydroxy-lower alkylene, hydroxyphenyl lower alkylene, amino-lower alkylene, guanidine lower alkylene, mercapto-lower alkylene, lower alkyl-mercapto-lower alkylene, imidazolyl lower alkylene, indolyl-lower alkylene or carbamoyl lower alkylene;

R₂ is hydrogen or lower alkyl;

R₃ is lower alkyl or phenyl lower alkylene;

R₄ is hydroxy, lower alkoxy or hydroxyamino; and n is 1 or 2.

U.S. Pat. No. 4,496,540 discloses compounds of the general formula:

wherein A is one of the aromatic group-containing amino acid residues L-tryptophyl, D-tryptophyl, L-tyrosyl, D-tyrosyl, L-phenylalanyl, or D-phenylalanyl, and B is one of the amino acids glycine, L-alanine, D-alanine, L-leucine, D-leucine, L-isoleucine, or D-isoleucine; and pharmaceutically acceptable salts thereof.

It would be desirable to improve on the solubility of known collagenase inhibitors and/or stromelysin inhibitors (whether as the free base or the salt) and, furthermore, increases in activity have also been sought. It is not a simple matter, however, to predict what variations in known compounds would be desirable to increase or even retain activity; certain modifications of known hydroxamic acid derivatives have been found to lead to loss of activity.

According to a first aspect of the invention, there is provided a compound of general formula I:

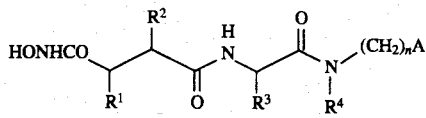

wherein:

R¹ represents a hydrogen atom or a $C_1-C_6$ alkyl, $C_1-C_6$ alkenyl, phenyl, phenyl($C_1-C_6$)alkyl, $C_1-C_6$ alkylthiomethyl, phenylthiomethyl, substituted phenylthiomethyl, phenyl($C_1-C_6$)alkylthiomethyl or heterocyclylthiomethyl group; or R¹ represents $—SR^x$ wherein $R^x$ represents a group

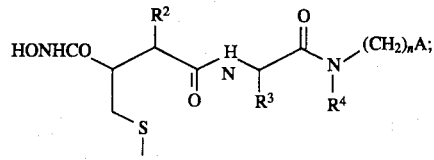

R² represents a hydrogen atom or a $C_1-C_6$ alkyl, $C_1-C_6$ alkenyl, phenyl($C_1-C_6$)alkyl, cycloalkyl($C_1-C_6$)alkyl, or cycloalkenyl ($C_1-C_6$)alkyl;

R³ represents an amino acid side chain or a $C_1-C_6$ alkyl, benzyl, ($C_1-C_6$)alkoxybenzyl, benzyloxy($C_1-C_6$)alkyl or benzyloxybenzyl group;

R⁴ represents a hydrogen atom or a methyl group;

n is an integer from 1 to 6; and

A represents the group $—NH_2$, a substituted acyclic amine or a heterocyclic base;

or a salt and/or N-oxide and/or (where the compound is a thio-compound) a sulphoxide or sulphone thereof.

Hereafter in this specification, the term "compound" includes "salt" unless the context requires otherwise.

As used herein the term "$C_1-C_6$ alkyl" refers to a straight or branched chain alkyl moiety having from one to six carbon atoms, including for example, methyl, ethyl, propyl, isopropyl, butyl, t-butyl, pentyl and hexyl, and cognate terms (such as "$C_1-C_6$ alkoxy") are to be construed accordingly.

The term "$C_1-C_6$ alkenyl" refers to a straight or branched chain alkyl moiety having one to six carbons and having in addition one double bond, of either E or Z stereochemistry where applicable. This term would include, for example, an alpha, beta-unsaturated methylene, vinyl, 1-propenyl, 1- and 2-butenyl and 2-methyl-2-propenyl.

The term "cycloalkyl" refers to a saturated alicyclic moiety having from 3 to 8 carbon atoms and includes, for example, cyclopropyl, cyclobutyl, cyclopentyl and cyclohexyl.

The term "cycloalkenyl" refers to an unsaturated alicyclic moiety having from 3 to 8 carbon atoms and includes, for example, cyclopropenyl, cyclobutenyl, cyclopentenyl and cyclohexenyl.

The term "substituted acyclic amine" refers to a group $—N(R^A)R^B$, wherein each of $R^A$ and $R^B$ independently represents a hydrogen atom or a $C_1-C_6$ alkyl group, with the proviso that at least one of $R^A$ and $R^B$ represents a $C_1-C_6$ alkyl group.

The term "heterocyclic base" refers to a group of general formula (II):

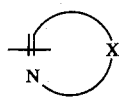

(II)

which represents a five or six membered saturated or unsaturated ring with or without an extra heteroatom (such as nitrogen and/or sulphur and/or oxygen) which may be fused to a benzene ring, for example pyridyl, imidazolyl, oxazolyl, thiazolyl, benzthiazolyl, benzoxazolyl, morpholinyl, pyrrolidinyl or piperidinyl. Preferred heterocyclic bases include pridyl, morpholinyl, piperidinyl and pyrrolidinyl.

The term "heterocyclylthiomethyl" refers to a methyl group substituted by a hetrocyclic thiol for example pyridine-2-thiol, pyridine-4-thiol, thiophene-2-thiol or pyrimidine-2-thiol.

The term "substituted", as applied to a phenyl or other aromatic ring, means substituted with up to four substituents each of which independently may be $C_1$–$C_6$ alkyl, $C_1$–$C_6$ alkoxy, hydroxy, thiol, $C_1$–$C_6$ alkylthiol amino, halo (including fluoro, chloro, bromo and iodo), triflouromethyl or nitro.

The term "amino acid side chain" means a characteristic side chain attached to the —$CH(NH_2)(COOH)$ moiety in the following R or S amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

There are several chiral centres in the compounds according to the invention because of the presence of asymmetric carbon atoms. The presence of several asymmetric carbon atoms gives rise to a number of diastereomers with the appropriate R or S stereochemistry at each chiral centre. General formula I and, where appropriate, all other formulae in this specification are to be understood to include all such stereoisomers and mixtures (for example racemic mixtures) thereof. Compounds in which the chiral centre adjacent the substituent $R^3$ has S stereochemistry are preferred.

Further or other preferred compounds include those in which, independently or in any combination:

$R^1$ represents a hydrogen atom or a $C_1$–$C_4$ alkyl (such as methyl), phenylthiomethyl or heterocyclylthiomethyl (such as thiophenylthiomethyl) group; p1 $R^2$ represents a $C_3$–$C_6$ alkyl (such as isobutyl or n-pentyl) group;

$R^3$ represents a benzyl, 4-($C_1$–$C_6$)alkoxyphenylmethyl or benzyloxy benzyl group;

$R^4$ represents a hydrogen atom:

n has the value 1, 2 or 3; and/or

A represents a morpholinyl (eg 4-morpholinyl), piperidinyl, 2-, 3- or 4-pyridyl or pyrrolidinyl group.

Particularly preferred compounds include:

1. [4-(N-Hydroxyamino)-2R-isobutylsuccinyl]-L-phenylalanine-N-[ (2-aminoethyl)-2(RS)-(1-methylpyrrolidine)] amide,
2. [4-(N-Hydroxyamino)-2R-isobutylsuccinyl]-L-phenylalanine-N-[ 1-(2-aminoethyl)-piperidine]amide,
3. [4-(N-Hydroxyamino)-2R-isobutylsuccinyl]-L-phenylalanine-N-[ 1-(2-aminoethyl)-pyrrolidine]amide,
4. [4-(N-Hydroxyamino)-2R-isobutylsuccinyl]-L-phenylalanine-N-[1-(3-aminopropyl)-2 (RS)-methylpiperidine] amide,
5. [4-(N-Hydroxyamino)-2R-isobutylsuccinyl]-L-phenylalanine-N-[ 2-(2-aminoethyl)-1-methylpyrrole]amide,
6. [4-(N-Hydroxyamino)-2R-isobutylsuccinyl]-L-phenylalanine-N-( 3-aminomethylpyridine)amide,
7. [4-(N-Hydroxyamino)-2R-isobutylsuccinyl]-L-phenylalanine-N-( 2-aminomethylpyridine)amide,
8. [4-(N-Hydroxyamino)-2(RS)-isobutylsuccinyl]-L-phenylalanine-N-( 4-aminomethylpyridine)amide,
9. [4-(N-Hydroxyamino)-2(RS)-isobutylsuccinyl]-L-phenylalanine-N-( 1-(3-aminopropyl)-imdazole)amide,
10. [4-(N-Hydroxyamino)-2(RS)-isobutylsuccinyl]-L-phenylalanine-N-( 2-aminomethylbenzimdazole)amide,
11. [4-(N-Hydroxyamino)-2R-isobutyl-3S-methylsuccinyl] -L-phenylalanine-N-[4-(2-aminoethyl)-morpholino] amide,
12. [4-(N-Hydroxyamino)-2R-isobutylsuccinyl]-L-phenylalanine-N-[ 4-(2-aminoethyl)-morpholine]amide,
13. [4-(N-Hydroxyamino)-2(R,S)-isobutylsuccinyl]-L-phenylalanine-N-[ 2-(2-aminoethyl)-pyridine]amide,
14. [4-(N-Hydroxyamino)-2(R,S)-isobutylsuccinyl]-L-phenylalanine-N-[ 4-(2-aminopropyl)-morpholine]amide,
15. [4-(N-Hydroxyamino)-2R-isobutylsuccinyl]-L-phenylalanine-N-( 3-aminomethylpyridine)amide hydrochloride,
16. [4-(N-Hydroxyamino)-2R-isobutylsuccinyl]-L-phenylalanine-N-[ 4-(2-aminoethyl)-morpholine]amide hydrochloride,
17. [4-(N-Hydroxyamino)-2(RS)-isobutylsuccinyl]-L-phenylalanine-N-( 4-aminomethylpyridine)amide hydrochloride,
18. [4-(N-Hydroxyamino)-2R-isobutyl-3S -methylsuccinyl] -L-phenylalanine-N-[4-(2-aminoethyl)-morpholine] amide hydrochloride and
19. [4-(N-Hydroxyamino)-2R-isobutyl-3S -methylsuccinyl] -L-phenylalanine-N-[4-(2-aminoethyl)-morpholine] amide sodium salt,
20. [4-(N-Hydroxyamino)-2R-isobutylsuccinyl]-1-phenylalanine-N-[ 1-(3-aminopropyl)-imidazole]amide
21. [4-(N-Hydroxyamino)-2R-isobutylsuccinyl]-1-phenylalanine-N-[ 2-(3-aminopropyl)-pyridine]amide
22. [4-(N-Hydroxyamino)-2R-isobutylsuccinyl]-1-phenylalanine-N-[ 2-aminoethyl)-N,N-diethylamine]amide
23. [4-(N-Hydroxyamino)-2R-isobutyl-3S-methylsuccinyl] -1-phenylalanine-N-[3-aminomethyl-pyridine]amide
24. [4-(N-Hydroxyamino)-2R-isobutyl-3S-methylsuccinyl] -1-phenylalanine-N-[4-aminomethyl-pyridine]amide
25. [4-(N-Hydroxyamino)-2R-isobutyl-3S-methylsuccinyl] -1-phenylalanine-N-[2-aminomethyl-pyridine]amide
26. [4-(N-Hydroxyamino)-2R-isobutyl-3S-methylsuccinyl] -1-phenylalanine-N-[2-(2-aminoethyl)-pyridine]amide
27. [4-(N-Hydroxyamino)-2R-isobutylsuccinyl]-1-phenylalanine-N-[ 2-(2-aminoethyl)-pyridine]amide hydrochloride
28. [4-(N-Hydroxyamino)-2R-isobutylsuccinyl]-1-phenylalanine-N-[ 4-aminomethyl-pyridine]amide hydrochloride
29. [4-(N-Hydroxyamino)-2R-isobutylsuccinyl]-1-phenylalanine-N-[ 2-aminomethyl-pyridine]amide hydrochloride
30. [4-(N-Hydroxyamino)-2R-isobutylsuccinyl]-1-phenylalanine-N-[ 2-(3-aminopropyl)-pyridine]amide hydrochloride
31. [4-(N-Hydroxyamino)-2R-isobutyl-3S-methylsuccinyl] -1-phenylalanine-N-[3-aminomethyl-pyridine] amide hydrochloride
32. [4-(N-Hydroxyamino)-2R-isobutyl-3S-methylsuccinyl] -1-phenylalanine-N-[2-(2-aminoethyl)-pyridine]amide hydrochloride
33. [4-(N-Hydroxyamino)-2R-isobutyl-3S-methylsuccinyl] -1-phenylalanine-N-[2-aminomethyl-pyridine] amide hydrochloride
34. [4-(N-Hydroxyamino)-2R-isobutyl-3S-methylsuccinyl] -1-phenylalanine-N-[4-aminomethyl-pyridine] amide sodium salt
35. [4-(N-Hydroxyamino)-2R-isobutyl-3S-methylsuccinyl] -1-phenylalanine-N-[2-(2-aminoethyl)-pyridine] amide sodium salt
36. [4-(N-Hydroxyamino)-2R-isobutyl-3S-methylsuccinyl] -1-phenylalanine-N-[3-aminomethyl-pyridine] amide sodium salt
37. [4-(N-Hydroxyamino)-2R-isobutylsuccinyl]-1-phenylalanine-N-[ 2-(3-aminopropyl)-pyridine]amide sodium salt
38. [4-(N-Hydroxyamino)-2R-isobutyl-3S-(phenylthiomethyl)succinyl] -L-phenylalanine-N-(2-methylpyridyl)amide and the free bases, free acids and salts thereof, where appropriate. Compounds 6 and 11 are especially preferred because of their good collagenase-inhibiting and protoglycanase inhibiting activities and compound 6 is the most preferred.

Compounds of general formula I may be prepared by any suitable method known in the art and/or by the following process, which itself forms part of the invention.

According to a second aspect of the invention, there is provided a process for preparing a compound of general formula I as defined above, the process comprising:

(a) deprotecting (for example by hydrogenating) a compound of general formula III

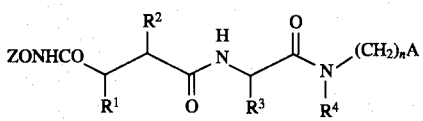

wherein:
$R^1$, $R^2$, $R^3$, $R^4$, n and A are as defined in general formula I and Z represents a protective group, such as a benzyl group; or (b) reacting a compound of general formula IV

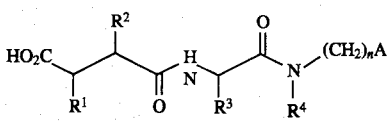

wherein:
$R^1$, $R^2$, $R^3$, $R^4$, n and A are as defined in general formula I, with the proviso that $R^1$ represents a hydrogen atom, with hydroxylamine or a salt thereof; and (c) optionally after step (a) or step (b) converting a compound of general formula I into another compound of general formula I.

Compounds of general formula I which are sulphoxides or sulphones can be derived from thiol compounds of general formula I by oxidation. Alternatively, thiols of general formula III or IV can be oxidised. Compounds of general formula I which are disulphides (ie compounds wherein $R^1$ represents $SR^x$) may be derived from thiol compounds of general formula I by mild oxidation with, for example, iodine in methanol.

A compound of general formula III can be obtained by coupling, for example by conventional coupling techniques, a compound of general formula IV with an O-protected (for example benzyl) hydroxylamine or by reacting a compound of general formula V

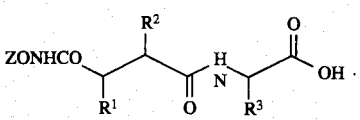

wherein:
$R^1$, $R^2$ and $R^3$ are as defined in general formula I and Z represents a protective group such as benzyl, with a compound of general formula VI

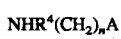

A compound of general formula V may be prepared by hydrolysis in the presence of a base such as sodium hydroxide of a compound of general formula VII

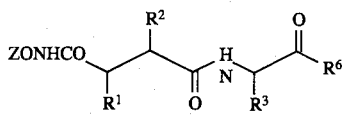

wherein:
$R^1$, $R^2$ and $R^3$ are as defined in general formula I, with the proviso that $R^1$ represents a hydrogen atom, $R^6$ represents a $C_1$–$C_6$ alkoxy, benzyloxy or substituted (eg 4-nitro) benzyloxy group, and Z represents a protective group.

A compound of general formula VII may be prepared by coupling, for example by conventional coupling techniques, a compound of general formula VIII with an O-protected (for example benzyl) hydroxylamine

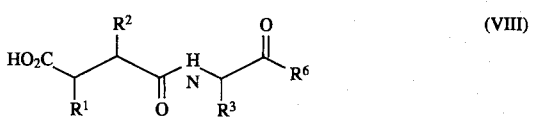

wherein:
$R^1$, $R^2$ and $R^3$ are as defined in general formula I and $R^6$ represents a $C_1$–$C_6$ alkoxy, benzyloxy or substituted benzyloxy group.

A compound of general formula VIII may be prepared by hydrogenating and (eg thermally) decarboxylating a compound of general formula IX

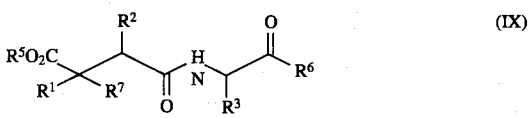

wherein:
$R^1$, $R^2$ and $R^3$ are as defined in general formula I, $R^5$ represents a $C_1$–$C_6$ alkyl or benzyl group, $R^6$ represents a $C_1$–$C_6$ alkoxy, benzyloxy or substituted benzyloxy group and $R^7$ represents a $C_1$–$C_6$ alkoxycarbonyl or benzyloxycarbonyl group.

A compound of general formula IX may be prepared by reacting a substituted acid of general formula X

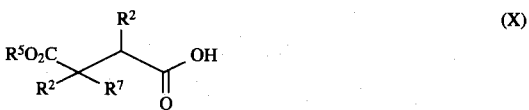

wherein:
$R^1$ and $R^2$ are as defined in general formula I, $R^5$ represents a $C_1$–$C_5$ alkyl or benzyl group and $R^7$ represents a $C_1$–$C_6$ alkoxycarbonyl or benzyloxycarbonyl group, with
an amino acid derivative of general formula (XI)

wherein:
$R^3$ is as defined in general formula I and $R^6$ represents a $C_1$–$C_6$ alkoxy, benzyloxy or substituted benzyloxy group.

Alternatively, a compound of general formula IV can be prepared by de-esterifying (for example hydrolysing, under acid or base catalysis) a compound of general formula XII

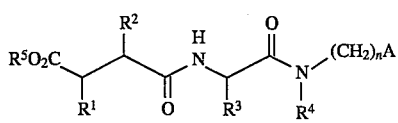

(XII)

wherein:

$R^1$, $R^2$, $R^3$, $R^4$, n and A are as defined in general formula I and $R_5$ represents a $C_1$–$C_6$ alkyl or benzyl group.

A compound of general formula XII can be prepared in a manner analogous to the preparation of a compound of formula IX by reacting a substituted acid of general formula XIII

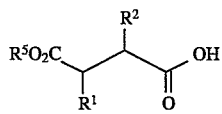

(XIII)

wherein:

$R^1$ and $R^2$ are as defined in general formula I and $R_5$ represents a $C_1$–$C_6$ alkyl or benzyl group, with an amino acid derivative of general formula XIV

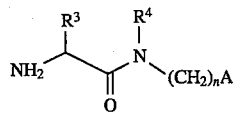

(XIV)

wherein:

$R^3$, $R^4$, n and A are as defined in general formula I.

In a further synthetic variant, a compound of general formula X as defined above wherein $R^1$ represents a hydrogen atom can be reacted with a compound of general formula XIV to produce a compound of general formula XV

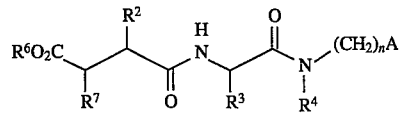

(XV)

wherein:

$R^2$, $R^3$ $R^4$, n and A are as defined in general formula I, $R^5$ represents a $C_1$–$C_6$ alkyl or benzyl group and $R^7$ represents a $C_1$–$C_6$ alkoxycarbonyl or benzyloxycarbonyl group.

A compound of general formula XV wherein $R^5$ represents benzyl and $R^1$ represents benzyloxycarbonyl may be hydrogenated to the malonic acid, then treatment with aqueous formaldehyde and piperidine gives a compound of formula XVI

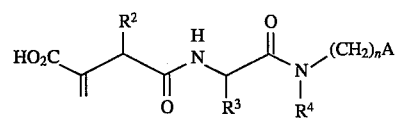

(XVI)

wherein:

$R^2$, $R^3$ $R^4$, n and A are as defined in general formula I.

Compounds of general formula XVI, by treatment with the appropriate thiols give the acids of general formula IV where $R^1$ is a substituted thiomethyl derivative. Thiomethyl derivatives can be oxidised to sulphoxides and sulphones as appropriate.

The starting materials (compounds of general formulae IX, X, XIII and XIV) and reagents described above are either commercially available or may be produced by conventional processes from commercially available materials. For example, when $R^1$ represents a hydrogen atom, the substituted acid of general formula XIII may be prepared by reaction of an aldehyde XVII

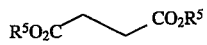

(XVII)

wherein $R^9$ represents a hydrogen atom or a $C_1$–$C_5$ alkyl $C_1$–$C_5$ alkenyl, phenyl ($C_1$–$C_5$) alkyl, cycloalkyl ($C_1$–$C_5$) alkyl or cycloalkenyl ($C_1$–$C_5$) alkyl group, with a succinate derivative of general formula XVIII,

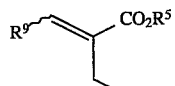

(XVIII)

wherein:

$R^5$ represents a $C_1$–$C_6$ alkyl or benzyl group under base catalysis to give a mixture of acids of general formulae XIXa and XIXb

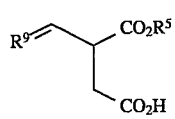

(XIXa)

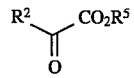

(XIXb)

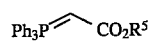

which by hydrogenation, esterification and hydrolysis can be converted to the acids of the general formula XIII.

Alternatively an ester of general formula XX may be reacted with an ester stablised phosphorane of general formula XXI

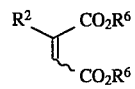

(XX)

(XXI)

to yield a compound of general formula XXII

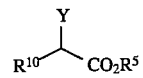

(XXII)

wherein $R^5$ represents a $C_1$–$C_6$ alkyl group, which can be further converted by hydrogenation to the acids of general formula XIII.

In addition the substituted esters may be prepared by reacting an ester of the general formula XXIII

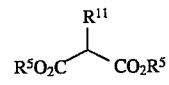

(XXIII)

wherein Y represents halo and $R^5$ is as defined above and $R^{10}$ is either $R^1$ or $R^2$ as defined above, with a malonate derivative of the general formula XXIV (XXIV)

wherein $R^{11}$ is $R^2$ or $R^1$ as defined above, and the alternative to that substituent employed in the halo ester.

Compounds of general formulae III and IV are valuable intermediates in the preparation of compounds of general formula I. According to a third aspect of the invention, there is therefore provided a compound of general formula III. According to a fourth aspect of the invention, there is provided a compound of general formula IV.

As mentioned above, compounds of general formula I are useful in human or veterinary medicine as they are active inhibitors, of metalloproteases involved in tissue degradation.

According to a fifth aspect of the invention, there is provided a compound of general formula I for use in human or veterinary medicine, particularly in the management (by which is meant treatment of prophylaxis) of disease involving tissue degradation, in particular rheumatoid arthritis, and/or in the promotion of wound healing.

According to a sixth aspect of the invention, there is provided the use of a compound of general formula I in the preparation of an agent for the management of disease involving tissue degradation, particularly rheumatoid arthritis, and/or in the promotion of wound healing. Compounds of general formula I can therefore be used in a method of treating disease involving tissue degradation, particularly rheumatoid arthritis, and/or in a method of promoting wound healing, the method in either case comprising administering to a human or animal patient an effective amount of a compound of general formula I.

The potency of compounds of general formula I to act as inhibitors of collagenase (a metalloprotease involved in tissue degradation) was determined by the procedure of Cawston and Barrett, (*Anal. Biochem.*, 99, 340–345, 1979) and their potency to act as inhibitors of stromelysin was determined using the procedure of Cawston et al (*Biochem. J.*, 195, 159–165 1981), both of which techniques are to be described more fully in the examples and, to the extent that the law allows, are incorporated by reference herein.

According to a seventh aspect of the invention, there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptable carriers and/or diluents and/or adjuvents and if desired other active ingredients.

According to an eighth aspect of the invention, there is provided a process for the preparation of a pharmaceutical or veterinary formulation in accordance with the seventh aspect, the process comprising admixing a compound of general formula I and a pharmaceutically and/or veterinarily acceptable carrier.

Compounds of general formula I may be formulated for administration by any route and would depend on the disease being treated. The may be in the form of tablets, capsules, powders, granules, lozenges, liquid or gel preparations, such as oral, topical, or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrollidone; fillers for example lactose, sugar, maize-starch, calcium phosphate, sorbitol or glycine; tableting lubricant, for example magnesium sterate, talc, polyethylene glycol or silica; disintegrants, for example potato starch, or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydrogenated edible fats; emulsifying agents, for example lecithin, sorbitan monooleate, or acacia; non-aqujeous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg, of a compound of general formula I. A suitable daily dose for a mammal may vary widely depending on the condition of the patient and will ultimately depend on the judgement of the physician or veterinarian. However, a dose of a compound of general formula I of about 0.1 to 300 mg/kg body weight, particularly from about 1 to 100 mg/kg body weight may be appropriate.

For topical application to the skin the drug may be made up into a cream, lotion or ointment. Cream or ointment formulations that may be used for the drug are conventional formulations well known in the art, for example, as described in standard text books of pharmaceutics such as the British Pharmacopoeia.

For topical applications to the eye, the drug may be made up into a solution or suspension in a suitable sterile aqueous or non-aqueous vehicle. Additives, for instance buffers such as sodium metabisulphite or disodium edeate; preservatives including bactericidal and fungicidal agents, such as phenyl mercuric acetate or nitrate, benzalkonium chloride or chlorohexidine, and thickening agents such as hypromellose may also be included.

The dosage employed for the topical administration will, of course, depend on the size of the area being treated. For the eyes each dose will be typically in the range from 10 to 100 mg of the compound of general formula I.

The active ingredient may also be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

For use in the treatment of rheumatoid arthritis the compounds of this invention can be administered by the oral route or by injection intra-articularly into the affected joint. The daily dosage for a 70 kg mammal will be in the range of 10 mgs to 1 gram of a compound of general formula I.

The following examples illustrate the invention, but are not intended to limit the scope in any way.

The following abbreviations have been used in the Examples:

DCC—Dicyclohexylcarbodiimide
DCM—Dichloromethane
DCU—Dicyclohexylurea
DIPE—Diisopropyl ether
DMF—N,N-dimethylformamide
HOBT—Hydroxybenztriazole
NMM—N-Methylmorpholine
TFA—Trifluoroacetic acid
THF—Tetrahydrofuran
WSCDI—N-(Dimethylaminoethyl)-N'-ethylcarbodiimide

EXAMPLE 1

[4-(N-Hydroxyamino)-2R-isobutylsuccinyl]-L-phenylalanine-N-[ (2-aminoethyl)-2(RS)-(1-methylpyrrolidine)]amide

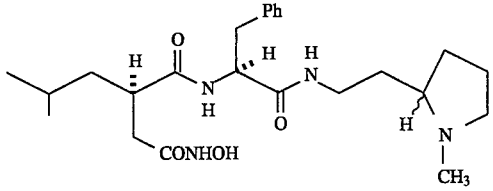

(a) [4-Benzyloxy-3-benzyloxycarbonyl-2R-isobutylsuccinyl] -L-phenylalanine methyl ester Benzyl (2-benzyloxycarbonyl-5-methyl-3R-tert-butoxycarbonyl)-hexanoate (52 g, 115 mmol) was stirred at room temperature with 5% water in TFA (250 ml) for 1.5 h. After this time the TFA was evaporated under reduced pressure then the residue was azeotroped with toluene (3×250 ml).

The crude acid from this reaction was dissolved in DCM/DMF (4:1), then HOBT (16 g, 118 mmol), NMM (12 g, 118 mmol) and WSCDI (22 g, 115 mmol) were added at room temperature. After 20 minutes a further equivalent of NMM (12 g, 118 mmol) was added followed by L-phenylalanine methyl ester hydrochloride (23 g, 107 mmol). This solution was stirred overnight and then concentrated under vacuum. The oily residue was dissolved in DCM then washed with 10% citric acid (2×250 ml), with 10% sodium bicarbonate (2×250 ml) and once with saturated brine (250 ml). The organic layer was dried (sodium sulphate), filtered then the solvent removed under reduced pressure to give the title compound as an oil (50.9 g, 79%).

delta$_H$ (250MHz, CDCl3) 7.39–7.11 (15H,m), 5.19 (2H, d, J=5Hz), 5.11 (2H, d, J=5Hz), 3.15–2.90 (2H, ABX), 0.79 (3H, d, J=6Hz), and 0.77 (3H, d, J=6Hz)

(b) Hydroxy-2R-isobutylsuccinyl]-L-phenylalanine methyl ester

The product from above (50.9 g, 91 mmol) was dissolved in ethanol (100 ml) and stirred at room temperature with activated charcoal pellets for 1 h. 10% Palladium on charcoal (20 g) in ethyl acetate was slurried into the ethanolic solution. Cyclohexene (20 ml) in ethanol (100 ml) was added and the mixture was brought to reflux for 5 h. The reaction mixture was filtered to remove the catalyst then the solvents evaporated under reduced pressure to leave a yellow oil (29.8 g). This oil was taken up in xylene (500 ml) and heated at reflux for 10 minutes. The xylene was removed under reduced pressure to leave the crude material as an oil (26.5 g).

(c) [4-(N-Benzyloxyamino)-2R-isobutylsuccinyl]-L-phenylalanine methyl ester

The crude acid (26.5 g, 79 mmol) was dissolved in DCM/DMF (4:1, 500 ml), then NMM (9.6 g, 95 mmol), HOBT (12.8 g 95 mmol) and WSCDI (18.2 g, 95 mmol) added and the mixture stirred at room temperature until tlc indicated complete conversion to the activated ester (about 10 minutes). To this solution containing the active ester was added benzylhydroxylamine hydrochloride (15.2 g, 95 mmol) and a further equivalent of NMM (9.6 g, 95 mmol) in the solvent mixture (80 ml). After stirring at room temperature overnight DCM (250 ml) was added then the mixture washed with citric acid (2×250 ml), 10% sodium bicarbonate solution (2×250 ml) and brine (250 ml) then finally dried over sodium sulphate. The solution was filtered and the solvent removed under reduced pressure to give an oil (27.2 g) which was purified by column chromatography using ether as an eluant to give the title compound (11 g, 23.7 mmol, 30%).

Delta$_H$ (250MHz, CDCl3) 7.47–7.09 (10H, m), 4.88 (2H, s), 3.11 (2H, d, J=6Hz), and 0.87 (6H, m)

(d) [4-(N-Benzyloxyamino)-2R-isobutylsuccinyl]-L-phenylalanine

[4-(N-Benzyloxyamino)-2R-isobutylsuccinyl]-L-phenylalanine methyl ester (9.5 g, 21 mmol) was dissolved in methanol (200 ml) and lithium hydroxide solution (0.5N, 84 ml, 42 mmol) was added with stirring at room temperature. When the reaction was complete, as judged from tlc, the methanol was removed by evaporation and the remaining aqueous phase was acidified to pH1 with citric acid. The precipitated solid was filtered off and dried, while the fitrate was extracted with DCM (500 ml) and dried over sodium sulphate. Solvent removal from the organic phase left an oil (5.38 g) which could be recrystallised from diisopropyl ether and methanol to give material which was identical with the solid which precipitated during acidification. These two batches were combined to give the title compound (6.40 g, 15 mmol, 71%)

m.p. 161°–162° C.

nu$_{max}$(KBr) 3300, 3020, 2980, 1710, 1650, 1630, 1550, 1265, 740, and 700 cm$^{-1}$ Delta$_H$ (250MHz, CDCl3/D6-DMSO) 7.36–7.18 (10H, m), 4.77 (2H, s), 3.14–2.91 (2H, ABX), 2.06–2.00 (2H, ABX), 1.50 (2H, bm), and 0.87–0.80 (6H, m)

Delta$_C$ (62.9MHz, D6-DMSO) 174.1, 173.1, 167.7, 137.9, 129.2–126.4, 76.9, 53.3, 40.7, 39.9, 36.8, 35.8, 25.3, 23.5, and 22.1

(e) [4-(N-Hydroxyamino)-2R-isobutylsuccinyl]-L-phenylalanine-N-[ (2-aminoethyl)-2(RS)-(1-methylpyrrolidine)]amide

[4-(N-Benzyloxyamino)-2R-isobutylsuccinyl]-L-phenylalanine (200 mg, 0.47 mmol) was dissolved in THF (6 ml) and cooled in ice. Triethylamine (52 mg, 0.522 mmol) was added together with ethylchloroformate (50 mg, 0.47 mmol) and after 10 minutes 2-(2-aminoethyl)-N-methylpyrrolidine (67 mg, 0.522 mmol) in THF (1 ml) was added. After 3 h at room temperature the reaction mixture was diluted with ethyl acetate then washed with sodium bicarbonate solution and brine, then dried over sodium sulphate. Solvent removal under reduced pressure gave the crude benzyl hydroxamate (220 mg, 0.41 mmol).

The crude material from above was dissolved in cyclohexene/ethanol (10% solution, 5 ml), 10% palladium on charcoal (50 mg) was added then the mixture refluxed until starting material had dissappeared by tlc (ca 30 minutes). The catalyst was removed by filtration, and the solvent removed under reduced pressure to leave an oil which could be crystallised by the addition of hexane. The required product (150 mg, 0.34 mmol, 72%) was collected by fitration.

m.p. 156°–158° C.

Analysis calculated for $C_{24}H_{38}N_4O_4 \cdot \frac{1}{2}H_2O$ Requires C 63.27 H 8.63 N 12.30 Found C 63.28 H 8.53 N 12.03 nu$_{max}$(KBr) 3300, 2950, 1650, 1550, and 700 cm$^{-1}$

Delta$_H$ (250MHz, CDCl$_3$) 7.19 (5H, m), 4.41 (1H, bm), 2.99 (2H, m), 2.01 (4H, m), 1.61 (4H, m), 1.30 (4H, m), and 0.72 (6H, m).

EXAMPLE 2

[4-(N-Hydroxyamino)-2R-isobutylsuccinyl]-L-phenylalanine-N-[ 1-(2-aminoethyl)-piperidine]amide

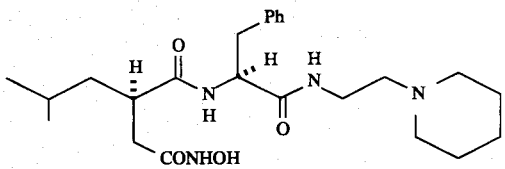

Using the procedure described in Example 1e [4-(N-benzyloxyamino)-2R-isobutylsuccinyl]-L-phenylalanine (200 mg, 0.47 mmol) was coupled with 1-(2-aminoethyl)-piperidine (67 mg, 0.522 mmol) then the product hydrogenated to give the title compound (66 mg, 0.15 mmol, 31%)

m.p. 154°–6° C. (DCM/hexane)

nu$_{max}$(KBr) 3300, 2950, 1640, 700 cm$^{-1}$

Delta$_H$ (250MHz, CDCl$_3$/D$_6$-DMSO) 7.2 (5H, s), 3.2 (1H, bm), 2.4 (5H, bm), 1.6 (3H, bd), 0.85 (6H, m)

EXAMPLE 3

[4-(N-Hydroxyamino)-2R-isobutylsuccinyl]-L-phenylalanine-N-[ 1-(2-aminoethyl)-pyrrolidine]amide

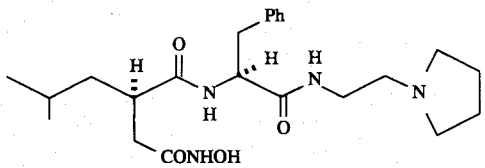

Using the procedure described in Example 1e [4-(N-benzyloxyamino)-2R-isobutylsuccinyl]-L-phenylalanine (200 mg, 0.47 mmol) was coupled with 1-(2-aminoethyl)-pyrrolidine (117 mg, 0.75 mmol) then the product hydrogenated to give the title compound.

m.p. 105°–110° C.

Analysis calculated for C$_{23}$H$_{36}$N$_4$O$_4$·0.4H$_2$O Requires C 62.82 H 8.43 N 12.74 Found C 63.09 H 8.18 N 12.23

Delta$_H$ (250MHz, D$_6$-DMSO) 8.14 (1H, d, J=8Hz, CONHCH), 7.78 (1H, t, J=5Hz, NHCH$_2$), 7.20 (5H, m, aromatic H), 4.42 (1H, m, PhCH$_2$CH), 3.10–2.62 (7H, m, NHCH$_2$CH$_2$, PhCH$_2$, and CHCH$_2$CO), 2.44–2.32 (6H, m, CH$_2$CH$_2$CH$_2$ and NHCH$_2$CH$_2$N), 1.62 (4H, m, CH$_2$CH$_2$CH$_2$), 1.30 (2H, m, CHCH$_2$CH), 0.98 (1H, m, (CH$_3$)$_2$CH), 0.74 and 0.78 (6H, 2xd, J=6Hz, (CH$_3$)$_2$CH).

EXAMPLE 4

[4-(N-Hydroxyamino)-2R-isobutylsuccinyl]-L-phenylalanine-N-[ 1-(3-aminopropyl)-2(RS)-methylpiperidine]amide

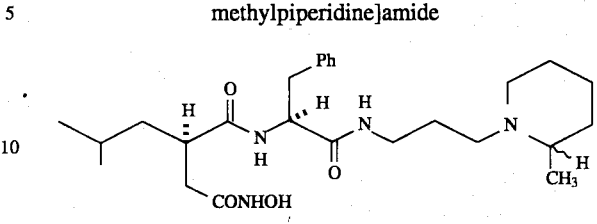

Using the procedure described in Example 1e [4-(N-benzyloxyamino)-2R-isobutylsuccinyl]-L-phenylalanine (200 mg, 0.47 mmol) was coupled with 1-(2-aminoethyl)-2-methylpiperidine (70 mg, 0.75 mmol) then the product hydrogenated to give the title compound.

m.p. 119°–124° C.

Delta$_H$ (250MHz, D$_6$-DMSO) 8.10 (1H, d, J=8Hz, CONHCH), 7.88 (5H, m, aromatic H), 4.38 (1H, m, PhCH$_2$CH), 3.10– 2.58 (7H, m, NHCH$_2$, PhCH$_2$, and COCH$_2$CHCO), 2.42–2.22 (5H, m, NCHCH$_2$CH$_2$CH$_2$CH$_2$ and NHCH$_2$CH$_2$CH$_2$N), 2.12–1.34 (8H, m, NCHCH$_2$CH$_2$CH$_2$CH$_2$ and NHCH$_2$CH$_2$ CH$_2$N), 1.24–1.16 (2H, m, CHCH$_2$CH), 1.00 (3H, d, J=4Hz, CH$_3$CHN), and 0.96–0.62 (7H, m, (CH$_3$)$_2$CH).

EXAMPLE 5

[4-(N-Hydroxyamino)-2R-isobutylsuccinyl]-L-phenylalanine-N-[ 2-(2-aminoethyl)-1-methylpyrrole]amide

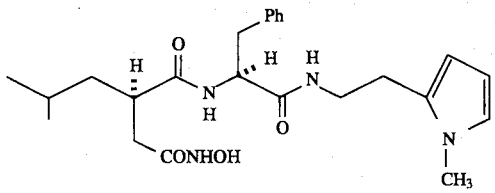

(a) Phenylalanine-N-[2-(2-aminoethyl)-1-methylpyrrole] amide

To a solution of N-(benzyloxycarbonyl)-phenylalanine (8.00 g, 26.7 mmol), 2-(2-aminoethyl)-1-methylpyrrole (3.65 g, 29.4 mmol), HOBT (3.98 g, 29.4 mmol) and NMM (2.97 g, 29.4 mmol) in DMF cooled to 0° was added a solution of DCC (6.07 g, 29.4 mmol) in THF. After addition was complete the reaction was left to stir at room temperature overnight. The solvents were removed under reduced pressure and the residual solid was taken up in ethyl acetate and washed with water, 10% sodium bicarbonate and brine then dried over sodium sulphate. Filtration and solvent removal gave the crude benzyloxy protected material which was converted to the free amine by dissolving in ethanol/cyclohexene (10% solution, 150 ml) adding 10% palladium on charcoal and refluxing for 2 h. This mixture was filtered to remove the catalyst, the ethanol was removed under reduced pressure, the residue dissolved in ethyl acetate and extracted with citric acid. Basification of the aqueous layer to pH 12 with sodium hydroxide solution was followed by extraction with ethyl acetate to give the title compound (4.11 g, 15 mmol, 57%)

Delta$_H$ (250MHz, CDCl3) 7.45–7.20 (7H, m, NH2+ aromatic H), 6.57 (1H, d, J=3Hz), 6.06 (1H, d, J= 4Hz), 5.89 (1H, m), 3.50 (5H, m), 3.28 (1H, m), 2.71 (2H, m), and 1.26 (2H, t, J=7Hz).

(b) [4-Benzyloxy-3-benzyloxycarbonyl-2R-isobutylsuccinyl]-L-phenylalanine-N-[2-(2-aminoethyl)-1-methylpyrrole] amide To a solution of phenylalanine-N-[2-(2-aminoethyl)-1-methylpyrrole]amide (2.00 g, 7.4 mmol), 4-tert-butyl-2R-isobutyl succinate (3.23 g, 8.1 mmol), HOBT (1.09 g, 8.1 mmol) and NMM (1.82 g, 8.1 mmol) in DMF cooled to 0° was added DCC (1.67 g, 8.1 mmol) in THF. The resultant mixture was allowed to warm to room temperature then stirring continued for 72 h. The precipitated DCU was collected by filtration then the solvents removed under reduced pressure. The residual oil was dissolved in ethyl acetate, washed with 10% sodium bicarbonate, water and brine then dried over sodium sulphate. Solvent removal under reduced pressure gave the crude product (5.48 g) as an oil. This material was purified by column chromatography using 40% ethyl acetate in hexane as eluant to give the desired isomer (1.45 g, 2.2 mmol, 30%) completely separated from the [4-benzyloxy-3-benzyloxycarbonyl-2S-isobutylsuccinyl] -L-phenylalanine-N-[2-(2-aminoethyl)-1-methyl pyrrole]amide isomer (1.04 g, 1.6 mmol, 22%).

Delta$_H$ (250MHz, CDCl$_3$) 7.27 (10H, m, aromatic H), 7.19 (5H, m), 6.54 (1H, m), 6.02 (1H, t, J=3Hz), 5.17– 5.01 (3H, m), 3.56 (3H, s), 3.31 (1H, m), 2.74 (2H, m), 1.68 (1H, bm), 0.97–0.74 (3H, bm), 1.65 (3H, d, j=6Hz), and 1.60 (3H, d, J=6Hz).

(c) [4-Hydroxy-2R-isobutylsuccinyl]-L-phenylalanine-N-[2-(2-aminoethyl)-1-methylpyrrole]amide

[4-Benzyloxy-3-benzyloxycarbonyl-2R-isobutylsuccinyl]-L-phenylalanine-N-[ 2-(2-aminoethyl)-1-methylpyrrole]amide (1.45 g, 2.3 mmol) was dissolved in ethanol/cyclonexene (10% solution), 10% palladium on charcoal (0.14 g) added and the mixture refluxed for 2 h. After this time tlc showed complete consumption of starting material so the reaction was cooled, filtered through celite and solvent removed under vacuum. The resultant oil was taken up in toluene and refluxed for two hours, solvent removal then gave the crude material (1.09 g, 2.6 mmol) which was used without further purification.

Delta$_H$ (250MHz, CDCl$_3$) 7.21 (5H, m), 6.53 (1H, m), 5.99 (1H, s), 3.57 (1H, s), 3.50 (3H, m), 3.38 (1H, bm), 2.59 (2H, m), 2.37 (3H, s), 1.54 (1H, m), 1.30 (1H, m), and 0.90 (6H, m).

(d) [4-(N-Benzyloxyamino)-2R-isobutylsuccinyl]-L-phenylalanine-N-[2-(2-aminoethyl)-1-methylpyrrole]amide

[4-Hydroxy-2R-isobutylsuccinyl]-L-phenylalanine-N-[2-( 2-aminoethyl)-1-methylpyrrole]amide (0.68 g, 1.6 mmol), benzylhydroxylamine (0.28 g, 1.8 mmol), NMM (0.18 g, 1.8 mmol) amd HOBT (0.24 g, 1.8 mmol) were dissolved in DMF and cooled to 0°. DCC (0.36 g, 1.8 mmol) in THF was added dropwise and when the addition was complete the mixture was allowed to stir overnight. The precipitated DCU was removed by filtration, the solvents removed from the filtrate under reduced pressure, the residue dissolved in ethyl acetate (50 ml) and washed with 10% sodium bicarbonate (2×50 ml), water (50 ml) and brine (50 ml) then dried over sodium sulphate. Filtration and removal of the ethyl acetate gave the crude product (1.25 g) as an oil. Further purification was achieved by column chromatography using 2% methanol/DCM as eluant to give the title compound (0.71 g, 1.34 mmol, 83%)

Delta$_H$ (250MHz, CDCl$_3$) 7.47–7.16 (10H, bm), 6.52 (1H, t, J=2Hz), 6.00 (1H, dd, J=3,4Hz), 5.75 (1H, m), 4.86 (2H, s), 3.44 (3H, s), 3.08 (2H, d, J=7Hz), 2.50 (2H, m), 1.46 (1H, m), and 0.85 (6H, m)

(e) [4-(N-Hydroxyamino)-2R-isobutylsuccinyl]-L-phenylalanine-N-[2-(2-aminoethyl)-1-methylpyrrole]amide

[4-(N-Benzyloxyamino)-2R-isobutylsuccinyl]-L-phenylalanine-N-[ 2-(2-aminoethyl)-1-methylpyrrole]amide (0.53 g, 1.0 mmol) was dissolved in cyclohexene/ethanol (10% solution, 20 ml), 10% palladium on charcoal (50 mg) was added then the mixture refluxed for 1 h. The catalyst was removed by filtration, and the solvent removed under reduced pressure to leave an oil which could be recrystalised from ethanol and diisopropyl ether. The required product (196 mg, 0.45 mmol, 45%) was collected by fitration.

m.p. 157°–158° C.

Delta$_H$ (250MHz, CDCl$_3$/D$_6$-DMSO) 8.06 (2H, d, J=2Hz), 7.97 (1H, m), 7.52 (5H, m, Ph), 6.87 (1H, d, J=1.8Hz, NH), 6.28 (1H, t, J=3Hz, NH), 6.27 (1H, s, NH), 3.89 (3H, s, N—CH$_3$), 3.70 (2H, m), 3.46 (3H, m), 2.98 (2H, m), 1.70 (2H, m), 1.43 (1H, m) and 1.20 (6H, m, 2xCH$_3$).

Delta$_C$ (62.9MHz, D$_6$-DMSO) 168.8, 165.6, 162.7, 132.5, 124.5, 123.7, 122.4, 120.6, 115.7, 100.9, 100.2, 72.1, 72.3, 73.5, 49.2, 36.3, 35.6, 35.0, 34.8, 34.0, 33.2, 32.3, 31.7, 30.4, 27.9, 23.9, 20.5, 19.7, 17.4, and 16.5

EXAMPLE 6

[4-(N-Hydroxyamino)-2R-isobutylsuccinyl]-L-phenylalanine-N-(3-aminomethylpyridine)amide

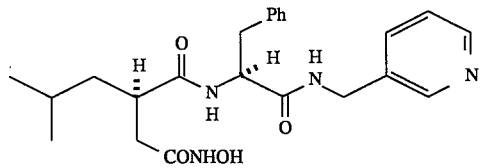

The title compound was prepared by the method described in Example 5 to give a compound with the following characteristics m.p. 184°–185°

[alpha]$_D$=+2.1° (c=1, MeOH)

nu$_{max}$(KBr) 3300, 1650, 1550, and 700 cm$^{-1}$

Analysis calculated for C$_{23}$H$_{30}$N$_4$O$_4$ Requires C 64.77 H 7.09 N 13.14 Found C 64.51 H 7.08 N 13.21

Delta$_H$ (250MHz, CDCl$_3$/D$_6$-DMSO) 8.68 (1H, bs), 8.41 (2H, m), 7.95 (1H, d, J=8Hz), 7.49 (1H, d, J=8Hz), 7.15 (5H, m, aromatic H), 4.46 (2H, m), 4.27 (2H, d, J= 6Hz), 3.09 (1H, dd, J=6, 14Hz), 2.88 (1H, dd, J=10, 14Hz), 2.12 (1H, dd, J=8, 16Hz), 1.95 (1H, dd, J=15, 6Hz), 1.30 (3H, m), and 0.70 (6H,m).

EXAMPLE 7

[4-(N-Hydroxyamino)-2R-isobutylsuccinyl]-
L-phenylalanine-N-( 2-aminomethylpyridine)amide

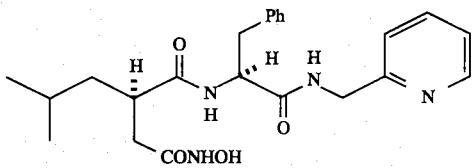

The title compound was prepared by the method described in Example 5 to give a compound with the following characteristics m.p. 165°–167° (decomp.)

[alpha]$_D$=+1.8° (c=0.83, MeOH)

nu$_{max}$(KBr) 3280, 2960, 2920, 1715, 1680, and 750 cm$^{-1}$

Delta$_H$ (250MHz, CDCl$_3$/D$_6$-DMSO, 1:3) 8.46 (2H, m), 8.05 (1H, partially obscured by solvent), 7.64 (1H, dt, J=2.8 Hz), 7.22 (7H, m), 4.56 (1H, m), 4.42 (1H, s), 4.40 (1H, s), 3.17 (1H, dd, J=5,14 Hz), 2.96 (1H, dd, J=9,14 Hz), 2.67 (1H, m), 2.16 (1H, dd, J=7,14 Hz), 2.00 (1H, dd, J=14,7 Hz), 1.37 (2H, m), 1.03 (1H, m), 0.79 (3H, d, J=6Hz), and 0.75 (3H, d, J=6 Hz).

Delta$_C$ (62.9MHz, CDCl$_3$/D$_6$-DMSO, 1:3) 174.2, 171.2, 167.9, 158.1, 148.4, 137.9, 136.3, 129.0, 127.9, 126.0, 121.7, 120.9, 78.7, 54.3, 44.3, 40.4, 37.0, 35.7, 25.2, 23.1, and 21.8.

EXAMPLE 8

[4-(N-Hydroxyamino)-2(RS)-isobutylsuccinyl]-
L-phenylalanine-N-( 4-aminomethylpyridine)amide

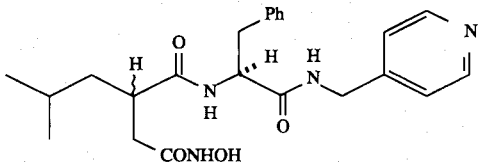

The title compound was prepared by the method described in Example 5 to give a 2:1 mixture of isomers with the following characteristics m.p. 189°–192° (decomp)

nu$_{max}$(KBr) 3320, 3250, 2960, 2925, 1655, 1640, 1610, 1540, 730, and 700 cm$^{-1}$ Delta$_H$ (250MHz, D$_6$-DMSO) includes 10.4 (1H, bs), 7.24 (5H, m), 7.11 (2H, d, J=6 Hz), 4.51 (1H, m), 4.28 (1H, s), 4.26 (1H, s), 0.76 (3H, d, J=6 Hz, major diastereomer), 0.72 (3H, d, J=6 Hz, major diastereomer), 0.69 (3H, d, J=6 Hz, minor diastereomer), 0.58 (3H, d, J=5 Hz, minor diastereomer)

Delta$_C$ (62.9MHz, D$_6$-DMSO) Major isomer 174.2, 171.5, 167.7, 149.4, 148.4, 138.2, 129.3, 128.2, 126.4, 122.1, 54.3, 41.2, 40.5, 40.1, 37.2, 35.8, 25.3, 23.5, and 22.0: Minor isomer 174.6, 171.7, 168.4, 149.5, 148.5, 138.6, 129.2, 128.1, 126.2, 122.2, 54.7, 41.5, 41.4, 40.9, 37.2, 36.8, 24.8, 23.6, and 21.9.

EXAMPLE 9

[4-(N-Hydroxyamino)-2(RS)-isobutylsuccinyl]-
L-phenylalanine-N-( 1-(3-amino-propyl)-imdazole)amide

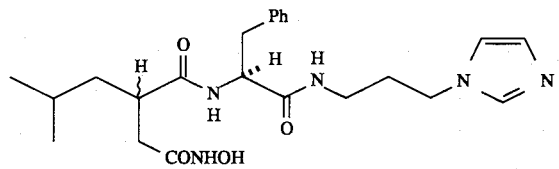

The title compound was prepared by the method described in Example 5 to give the title compound with the following characteristics m.p. 166–167

Delta$_H$ (250MHz, CDCl$_3$) 7.35 (1H, m), 7.28–7.15 (5H, m), 7.14 (1H, m), 7.00 (1H, s), 6.88 (1H, s), 4.97 (1H, m), 4.00–3.90 (2H, m), 3.55–3.34 (2H, m), 3.32 (1H, m), 3.14 (1H, m), 2.59 (2H, m), 2.08 (2H, m), 1.94 (2H, m), 1.52 (1H, sep, J=7Hz), 1.29 (1H, m), and 0.91–0.73 (6H, m).

Delta$_C$ (62.9MHz, CDCl$_3$) 179.8, 177.0, 168.7, 137.6, 137.0, 129.2, 128.6, 126.8, 118.6, 116.0, 77.6, 77.2, 76.6, 55.4, 44.5, 40.3, 38.1, 37.2, 34.6, 33.7, 30.6, 25.8, 22.8, and 21.7.

(e) [4-(N-Hydroxyamino)-2R-isobutylsuccinyl]-
L-phenylalanine-N-[ 2-(2-aminoethyl)-1-methylpyrrole]amide

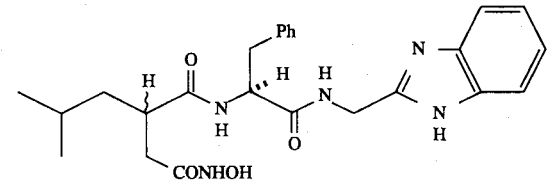

The title compound was prepared by the method described in Example 5 to give the title compound with the following characteristics m.p. 217°

[alpha]$_D$=-77.4° (c=1, MeOH)

nu$_{max}$(KBr) 3280, 2960, 2920, 2860, 1650, 1550, 1510, 1440, 1275, 1030, 740, and 700 m$^{-1}$ Delta$_H$ (250MHz, CDCl$_3$/D$_4$ Methanol) 8.4 (1H, s, NH), 7.34 (2H, m), 7.26 (1H, s), 7.05 (5H, m), 4.48 (2H, m), 3.27 (1H, dd, J=10,4Hz), 3.17 (3H, m), 2.67–2.48 (2H, m), 2.20–1.92 (2H, m), 1.18 (1H, m), 0.73 (1H, m), and 0.52 (6H, m, (CH$_3$)$_2$CH)

Delta$_C$ (62.9MHz, CDCl$_3$/D$_4$ Methanol) 171.1, 167.4, 164.7, 143.8, 132.0, 123.4, 123.1, 121.3, 117.3, 49.3, 36.3, 35.5, 31.6, 31.4, 30.2, 19.8, 17.8, and 16.0

(e) [4-(N-Hydroxyamino)-2R-isobutyl-succinyl]-L-phenylalanine-N-[2-(2-aminoethyl)-1-methylpyrrole]amide

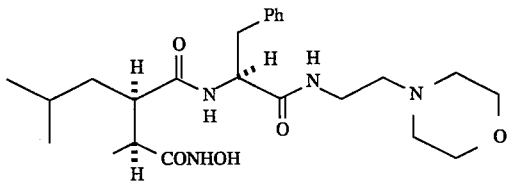

(a) Phenylalanine-N-[4-(2-aminoethyl)morpholino]amide

To a solution of N-(Benzyloxycarbonyl)-phenylalanine (29.91 g, 100 mmol), 4-(2-aminoethyl)-morpholine (14.32 g, 110 mmol), HOBT (14.86 g, 110 mmol) and NMM (11.13 g, 110 mmol) in DCM/DMF (4:1) and DCC (6.07 g, 29.4 mmol) added. After addition was complete the reaction was left to stir at room temperature overnight. The solvents were removed under reduced pressure and the residual solid was taken up in ethyl acetate and washed with water, 10% aodium bicarbonate and brine. The ethyl acetate layer was then extracted with 3% hydrochloric acid the aqueous solution separated and basified to pH 11. This solution was extracted with ethyl acetate, dried over sodium sulphate then solvent removal gave the amine as a crude solid which was recrystallised from ethyl acetate/hexane (44.78 g, 109 mmol, 100%).

$Delta_H$ (250MHz, $CDCl_3$) 7.56 (1H, m), 7.45 (5H, m), 7.39 (5H, bs), 7.15 (1H, d, J=8Hz), 5.17 (2H, s), 4.49 (1H, q, J=7Hz), 3.75 (3H, m), 3.40 (2H, t, J=6Hz), 3.24 (1H, dd, J=5.5,14Hz), 3.05 (1H, m), and 2.51 (4H, bs).

$Delta_C$ (62.9MHz, $CDCl_3$) 170.6, 136.8, 136.3, 129.4, 128.7, 128.6, 128.3, 128.1, 127.0, 77.7, 77.2, 76.6, 67.0, 66.7, 56.7, 56.4, 53.1, 39.3, and 35.5.

This material was converted to the free amine by dissolving in ethanol/cyclohexene (10% solution), adding 10% palladium on charcoal and refluxing for 2 h. The mixture was filtered to remove the catalyst, then the ethanol was removed under reduced pressure to give the title compound (19.16 g, 69 mmol, 69%).

(b) [4-tert-Butoxy-2R-isobutyl-3S-methyl-succinyl]-L-phenylalanine-N-[4-(2-aminoethyl)-morpholine]amide To a solution of phenylalanine-N-[4-(2-aminoethyl)-morpholine]amide (19.16 g, 69 mmol), 4-tert-butyl-2R-isobutyl succinate (18.57 g, 76 mmol), HOBT (10.27 g, 76 mmol) and NMM (7.69 gg, 76 mmol) in DMF cooled to 0° was added DCC (15.68 g, 76 mmol) in THF. The resultant mixture was allowed to warm to room temperature then stirring continued over the weekend. The precipitated DCU was collected by filtration then the solvents removed under reduced pressure. The residual oil was dissolved in ethyl acetate, washed with 10% sodium bicarbonate, water and brine then dried over sodium sulphate. Solvent removal under reduced pressure gave the crude product (36.5 g) as an oil. This material was purified and the diastereomers separated by careful column chromatography using 0–5% methanol in DCM as eluant to give the desired isomer slightly contaminated with a lower running isomer (7.36 g, 15.6 mmol, 23%)

$Delta_H$ (250MHz, $CDCl_3$) 7.23 (5H, m), 6.54 (1H, d, J=6.5Hz), 6.04 (1H, m), 3.60 (4H, m), 3.22–3.08 (2H, m), 2.95 (1H, m), 2.44–2.20 (8H, m), 1.71 (1H, m), 1.43 (9H, m), 1.12 (1H, m), 0.95 (2H, d, J=6Hz), and 0.83 (6H, t, J=6Hz).

(c) [4-(N-Benzyloxyamino)-2R-isobutyl-3S-methylsuccinyl]-L-phenylalanine-N-[4-(2-aminoethyl)-morpholine]amide

[4-tert-Butoxy-2R-isobutyl-3S-methylsuccinyl]-L-phenylalanine-N-[ 4-(2-aminoethyl)-morpholine]amide (2.37 g, 4.7 mmol) was dissolved in 5% water in TFA (15 ml) with cooling and stirred for 90 minutes after which time tlc indicated that deprotection was complete. Removal of the excess TFA was achieved by azeotroping with xylene to give the crude acid which was used without further purification. This product was taken up in DCM/DMF (4:1, 20 ml) and the pH adjusted to 7 by adding NMM. To this was added HOBT (0.76 g, 5.6 mmol) and NMM (0.57 g, 5.6 mmol), then after cooling to 0°, WSCDI (1.08 g,5.6 mmol). This mixture was left to stir at room temperature for 45 minutes, cooled in an ice bath and benzylhydroxylamine (0.90 g, 5.6 mmol) added and finally stirred overnight. The precipitated product was filtered off and dried to yield the title compound as a single isomer (1.62 g, 2.9 mmol, 52%).

$Delta_H$ (250MHz, $D_6$-DMSO) 8.26–8.23 (1H, d, J=8Hz), 7.70 (1H, t, J=4Hz), 7.35 (5H, bs), 7.29–7.23 (5H, m), 4.74 (2H, s), 4.56 (1H, m), 3.55 (4H, t, J=5Hz), 3.34 (5H, bs), 3.16 (2H, q, J=6Hz), 2.90 (1H, m), 2.77 (1H, m), 2.33 (4H, t, J=5Hz), 2.27–2.25 (2H, m), 1.94 (1H, m), 1.30–1.26 (2H, m), 0.80 (3H, d, J=6Hz), 0.72 (3H, d, J=6Hz), and 0.42 (3H, d, J=7Hz).

(d) [4-(N-Hydroxyamino)-2R-isobutyl-3S-methylsuccinyl]-L-phenylalanine-N-[4-(2-aminoethyl)-morpholine]amide

[4-(N-Benzyloxyamino)-2R-isobutyl-3S-methylsuccinyl] -L-phenylalanine-N-[ 4-(2-aminoethyl)-morpholine]amide (8.1 g, 14.6 mmol) was dissolved in ethanol/cyclohexene (10% solution, 100 ml), 10% palladium on charcoal (1.5 g, 20% wt/wt) added and the mixture refluxed for 30 minutes. Filtratiion to remove catalyst followed by solvent removal under reduced pressure gave a white solid which was recrystallised from 5% methanol in ethyl acetate. Drying gave the title compound (5.3 g, 11.5 mmol, 78%).

m.p. 205°–210° C.

Analysis calculated for $C_{24}H_{38}N_4O_5$ Requires C 62.32 H 8.28 N 12.11 Found C 62.05 H 8.22 N 11.97

$Delta_H$ (250MHz, $D_6$-DMSO) 8.76 (1H, s, NHOH), 8.22 (1H, d, J=8Hz, CONHCH), 7.72 (1H, bs, NHCH$_2$), 7.38–7.04 (5H, m, aromatic H), 4.56 (1H, m, PhCH$_2$CH), 3.64–3.42 (4H, m, CH$_2$OCH$_2$), 3.18 (2H, d, J=5Hz, NHCH$_2$), 2.98–2.70 (2H, m, PhCH$_2$), 2.44–2.10 (8H, m, NHCH$_2$CH$_2$ and CH$_2$NCH$_2$), 1.31 (2H, m, CH$_2$CH), 0.87–0.71 (7H, m, (CH$_3$)$_2$CH), and 0.41 (3H, d, J=6Hz, CH$_3$CH).

$Delta_C$ (62.9MHz, $D_6$-DMSO) 173.5 (CONHOH), 171.2 (CONHCONH), 138.2–126.2 (Aromatic C), 66.3 (CH$_2$OCH$_2$), 57.3 (PhCH$_2$CH), 54.1 (NHCH$_2$CH$_2$), 53.4 (CH$_2$NC$_H$2), 46.8 (NHCH$_2$), 37.4 (PhCH$_2$ and CHCHCO), 36.0 (CH$_2$CH), 25.4 (Me2CH), 24.2, 21.7 ((CH$_3$)$_2$CH), and 16.1 (CH$_3$CH).

EXAMPLE 12

[4-(N-Hydroxyamino)-2R-isobutylsuccinyl]-L-phenylalanine-N-[4-(2-aminoethyl)-morpholine]amide

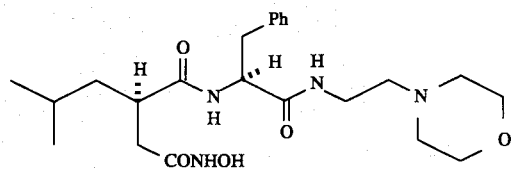

(a) [4-tert-Butoxy-2(RS)-isobutylsuccinyl]-L-phenylalaninebenzyl ester

To a solution of phenylalanine benzyl ester tosic acid salt (6.74 g 17.6 mmol), 4-tert-butyl-2(RS)-isobutyl succinate (3.68 g, 16.0 mmol), HOBT (2.38 g, 17.6 mmol) and NMM (1.78 g, 17.6 mmol) in DMF (20 ml) at 0° was added a solution of DCC (3.63 g, 17.6 mmol) in THF (20 ml). The resultant mixture was allowed to warm to room temperature then stirred overnight. The precipitated DCU was removed by filtration then the solution concentrated under reduced pressure. The residual oil was taken up in ethyl acetate and washed sequentitally with 10% sodium bicarbonate, dilute hydrochloric acid, water and finally brine. The solution was dried over sodium sulphate and the ethyl acetate removed under reduced pressure. The crude material thus produced was purified by column chromatography using gradient elution of ethyl acetate in DCM (0–15%) to give the title compound (3.16 g, 6.7 mmol, 42%)

(b) [4-tert-Butoxy-2(RS)-isobutylsuccinyl]-L-phenylalanine

[4-tert-Butoxy-2(RS)-isobutylsuccinyl]-L-phenylalanine benzyl ester (3.16 g, 6.7 mmol) was dissolved cyclohexene/ethanol (10% solution, 50 ml), 10% palladium on charcoal (2.0 g) added and the mixture refluxed for 10 minutes. The cooled solution was filtered through celite and the solvent removed to leave the title compound (2.25 g, 6.0 mmol, 89%).

Delta$_H$ (250MHz, CDCl$_3$) 7.27–7.16 (5H, m), 6.32 (1H, m), 4.88 (1H, m), 3.18 (2H, m), 2.61 (2H, m), 2.33 (1H, m), 1.45–1.42 (9H, 2xs), 1.27–1.21 (2H, m), and 0.88–0.82 (6H, m).

(c) [4-tert-Butoxy-2(RS)-isobutylsuccinyl]-L-phenylalanine-N-[4-(2-aminoethyl)-morpholine]amide 4-tert-Butoxy-2(RS)-isobutylsuccinyl]-L-phenylalanine (2.27 g, 6.01 mmol), HOBT (0.89 g,6.62 mmol), NMM (0.67 g, 6.62 mmol) and 4-(2-aminoethyl)-morpholine (0.86 g, 6.62 mmol) were dissolved in DCM/DMF (4:1, 50 ml) and cooled to 0° while WSCDI (1.27 g, 6.62 mmol) was added. After addition was complete the reaction was allowed to warm to room temperature and then stirred overnight. Solvents were removed under reduced pressure then the residual oil taken up in ethyl acetate and washed with water (200 ml) and brine (200 ml). Drying the organic layer with sodium sulphate, filtration and solvent removal gave desired compound as a mixture of diastereomers (1.85 g, 3.8 mmol) which was deprotected without further purification.

Delta$_H$ (250MHz, CDCl$_3$) 7.18 (5H, m), 7.16 (1H, m), 6.48 (1H, m), 3.59 (4H, t, J=4.5Hz), 3.44 (1H, m), 3.24–3.02 (2H, m), 2.43 (1H, m), 2.36 (8H, m), 2.11 (1H, m), 1.35 (9H, s), 1.09 (1H, d, J=1Hz), 1.06 (1H, d, J= 1Hz), and 0.72–0.69 (6H, m, 2xCH$_3$)

(d) [4-(N-Benzyloxyamino)-2(RS)-isobutylsuccinyl]-1-phenylalanine-N-[4-(2-aminoethyl)-morpholine]amide

[4-tert-Butoxy-2(RS)-isobutylsuccinyl]-L-phenylalanine-N-[ 4-(2-aminoethyl)-morpholine]amide (1.84 g, 3.5 mmol) was dissolved in water in TFA (5% solution, 20 ml) and stirred for 2 h at room temperature. The excess TFA was removed by azeotroping with xylene to give the crude acid. This material was mixed with HOBT (0.57 g, 4.15 mmol), benzylhydroxylamine hydrochloride (0.67 g, 4.18 mmol) and NMM (0.42 g, 4.18 mmol) and dissolved in DCM/DMF (4:1, 35 ml) and cooled to 0° while WSCDI (0.80 g, 4.18 mmol) was added. The mixture was warmed to room temperature and stirred overnight then solvent removed under reduced pressure to leave an oily residue.

Delta$_H$ (250MHz, D$_6$-DMSO) 8.00 (1H, m), 7.53 (5H, m), 7.38 (5H, bs), 4.98 (1H, s), 3.79–3.75 (4H, t, J= 5Hz), 3.41 ((4H, s), 2.54 (8H, m), and 0.99–0.95 (6H, 2xd, J=6Hz).

(e) [4-(N-Hydroxyamino)-2(RS)-isobutylsuccinyl]-L-phenylalanine-N-[4-(2-aminoethyl)-morpholine]amide

[4-(N-Benzyloxyamino)-2(RS)-isobutylsuccinyl]-1-phenylalanine-N-[ 4-(2-aminoethyl)-morpholine]amide (250 mg, 0.46 mmol), was dissolved in cyclohexene/ethanol (10%, 5 ml) and to it was added 10% palladium on charcoal (250 mg). The mixture was refluxed for 1 h at room temperature, then the cooled solution fitered through glass wool. The solvent was then removed under reduced pressure to leave an oily solid which was recrystallised from ethanol and DIPE (131 mg, 0.30 mmol, 64%)

m.p. 151°–153° C.

Delta$_H$ (250MHz, CDCl$_3$) 8.02 (2H, m), 7.55 (1H, m), 7.39 (5H, bs), 4.69 (1H, m), 3.31–3.28 (4H, m), 3.14 (1H, m), 2.63–2.54 (8H, m), 1.26 (1H, m), and 1.01–0.97 (6H, m).

Delta$_C$ (62.9MHz, CDCl$_3$) 174.1, 171.0, 167.5, 138.3, 129.2, 128.1, 126.2, 66.3, 57.3, 54.1, 53.4, 37.4, 36.1, 25.3, 23.5, and 22.0

EXAMPLE 13

[4-(N-Hydroxyamino)-2(R,S)-isobutylsuccinyl]-L-phenylalanine-N-[2-(2-aminoethyl)-pyridine]amide

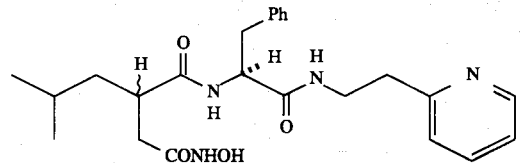

The title compound was prepared by the method described in Example 12 to give a compound with the following characteristics m.p. 174°–175° nu$_{max}$(KBr) 3300, 2900, 1700, 1650, 1550, and 700 cm$^{-1}$

Analysis calculated for $C_{24}H_{32}N_4O_4.0.2H_2O$ Requires C 64.90 H 7.35 N 12.61 Found C 64.90 H 7.35 N 12.76

$Delta_H$ (250MHz, $D_6$-DMSO) 8.88 (1H, bm), 8.49 (2H, d, J=4Hz), 8.36 (1H, d, J=9Hz), 8.03 (2H, m), 7.70 (1H, m), 7.21 (5H, m), 4.39 (1H, m), 3.46 (4H, m), 2.83 (4H, m), 2.17 (1H, dd, J=9,15 Hz), 1.92 (1H, dd, J= 12,3 Hz), and 0.76 (6H, m)

(e) [4-(N-Hydroxyamino)-2(RS)-isobutylsuccinyl]-L-phenylalanine-N-[4-(2-aminoethyl)-morpholine]amide

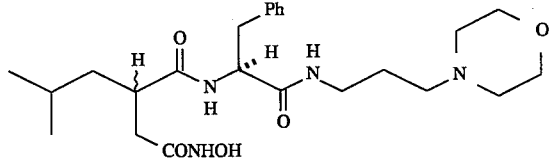

The title compound was prepared by the method described in Example 12 to give a compound with the following characteristics m.p. 140°–142° C.

$Delta_H$ (250MHz, $CDCl_3/D_6$-DMSO, 60:40) 8.15 (1H, d, J=9Hz), 8.03 (1H, s), 7.93 (1H, t, J=4.5Hz), 7.58–7.56 (5H, m), 6.92 (1H, t, J=4Hz), 4.02 (4H, m), 3.73 (1H, dd, j=4,14Hz), 3.50–3.44 (2H, m), 2.85 (1H, m), 2.78–2.66 (4H, m), 2.42 (2H, dd, J=5,15Hz), 1.64 (1H, m), 1.26–1.08 (2H, m), 1.04 (3H, d, J=5Hz), and 0.95 (3H, d, J=6Hz).

EXAMPLE 15

[4-(N-Hydroxyamino)-2R-isobutylsuccinyl]-L-phenylalanine-N-(3-aminomethylpyridine)amide hydrochloride

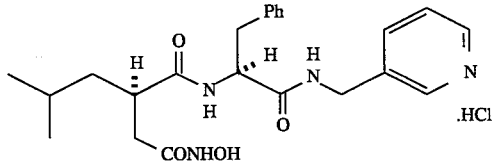

[4-(N-Hydroxyamino)-2R-isobutylsuccinyl]-L-phenylalanine-N-( 3-aminomethylpyridine)amide (100 mg, 0.23 mmol) was dissolved in hydrochloric acid (2.34 ml, 0.1M) then the solution freeze dried to leave the title compound as a white solid (64 mg, 0.14 mmol, 60%).

m.p. 87°

$[alpha]_D=-32.2$ (c=1, MeOH)

$nu_{max}$(KBr) 3300–3200, 3060, 2955, 2860, 1650, 1530, 1470, 1385, 700 and 680 cm$^{-1}$ $Delta_H$ (250MHz, $CDCl_3/D_4$-Methanol) 9.30 (1H, s), 8.50 (1H, t, J=4Hz), 8.45 (1H, s), 8.42 (1H, d, J= 3Hz), 8.10 (1H, d, J=6Hz), 7.65 (1H, t, J=4Hz), 6.99 (5H, m), 4.20 (2H, m), 3.09 (2H, m), 3.02 (1H, d, J= 4Hz), 2.86 (1H, m), 2.38 (1H, m), 2.13 (1H, m), 1.93 (1H, dd, J=3,10Hz), 1.08–1.02 (1H, m), 1.02–0.81 (2H, m) and 0.45 (6H, 2xd, J=7Hz).

$Delta_C$ (62.9MHz, $CDCl_3/D_4$-Methanol) 175.8, 172.0, 168.8, 144.3, 140.7, 139.8, 136.9, 128.6, 128.0, 126.3, 55.3, 41.4, 41.0, 39.6, 35.8, 35.1, 24.9, 22.2, and 21.1.

EXAMPLE 16

[4-(N-Hydroxyamino)-2R-isobutylsuccinyl]-L-phenylalanine-N-[4-(2-aminoethyl)-morpholine]amide hydrochloride

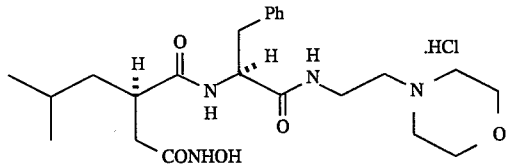

The title compound was prepared by the method described in Example 15 to give a compound with the following characteristics $[alpha]_D=-37.5$ (c=1, MeOH)

$nu_{max}$(KBr) 3450–3250, 2960, 2870, 1650, 1525, 1450, and 1100 cm$^{-1}$ $Delta_H$ (250MHz, $CDCl_3/D_4$-Methanol) 7.33 (5H, m, Aromatic H), 4.75 (1H, s), 3.90 (2H, m), 3.45 (2H, m), 3.20–3.00 (4H, m), 2.74 (1H, t, J=Hz), 2.28 (2H, m), 1.50–1.10 (3H, m), and 0.82 (6H, m, 2xMe).

EXAMPLE 17

[4-(N-Hydroxyamino)-2(RS)-isobutylsuccinyl]-L-phenylalanine-N-(4-aminomethylpyridine)amide hydrochloride

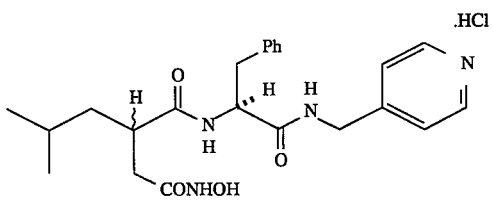

The title compound was prepared by the method described in Example 15 to give a compound with the following characteristics $[alpha]_D=-22.7$ (c=1, MeOH)

$nu_{max}$(KBr) 3300–3200, 3160, 2960, 1640, 1550–1500, 1410, 1380, 1365, 1250, and 600 cm$^{-1}$ Analysis calculated for $C_{23}H_{31}N_4O_4Cl$ Requires C 59.67 H 6.75 N 12.10 Found C 57.01 H 6.59 N 11.27

$Delta_H$ (250MHz, $D_4$-Methanol) 8.74 (2H, dd, J=10,3Hz), 7.96 (1H, d, J=7Hz), 7.90 (2H, d, J=7Hz), 7.84 (2H, d, J=7Hz), 7.28 (5H, m), 4.76 (1H, s), 4.65 (2H, s), 4.50 (1H, dd, J=9,6Hz), 3.28 (1H, m), 3.12 (1H, m) 2.70 (1H, m), 2.37 (1H, m), 2.15 (1H, m), 1.34 (2H,m), 0.97 (1H, m), and 0.82 (6H, m, 2xMe).

$Delta_C$ (62.9MHz, $D_4$-Methanol) 177.7, 174.4, 170.8, 162.3, 142.4, 130.2, 129.9, 129.5, 127.7, 126.5, 126.4, 56.8, 43.4, 42.7, 37.5, 36.6, 26.5, 23.4, and 22.2

EXAMPLE 18

[4-(N-Hydroxyamino)-2R-isobutyl-3S-methyl-succinyl]-L-phenylalanine-N-[4-(2-aminoethyl)-morpholine]amide hydrochloride

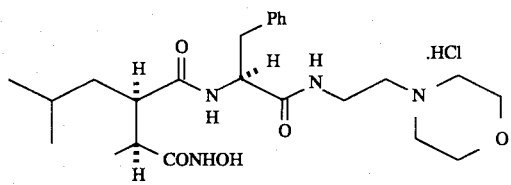

The title compound was prepared by the method described in Example 15 to give a compound with the following characteristics Analysis calculated for $C_{24}H_{39}N_4O_5Cl$ Requires C 55.75 H 7.99 N 10.84 Found C 55.65 H 7.81 N 10.81

$Delta_H$ (250MHz, $D_6$-DMSO) 10.52 (1H, m, O$\underline{H}$), 8.22 (2H, m, CON$\underline{H}$ and CON$\underline{H}$), 7.02–7.40 (5H, m, Aromatic H), 4.50 (1H, m, C$\underline{H}$CH$_2$Ph), 4.04–3.82 (4H, m, C$\underline{H}_2$OC$\underline{H}_2$), 3.46–2.72 (12H, m, NHC$\underline{H}_2$C$\underline{H}_2$, C$\underline{H}_2$NC$\underline{H}_2$, PhC$\underline{H}_2$, and NHC$\underline{H}_2$), 2.40–1.96 (2H, m, C$\underline{H}$C$\underline{H}$CO), 1.38 (2H, m, CHC$\underline{H}_2$CH), 1.00–0.84 (7H, m, C$\underline{H}$(C$\underline{H}_3$)$_2$), and 0.42 (3H, d, J+ 4Hz, C$\underline{H}_3$CH).

EXAMPLE 19

[4-(N-Hydroxyamino)-2R-isobutyl-3S-methylsuccinyl]-L-phenylalanine-N-[4-(2-aminoethyl)-morpholine]amide sodium salt.

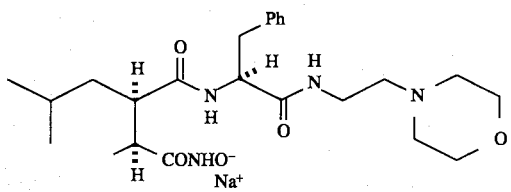

[4-(N-Hydroxyamino)-2R-isobutyl-3S-methylsuccinyl]-L-phenylalanine-N-[ 4-(2-aminoethyl)-morpholine]amide (92.4 mg, 0.2 mmol) was dissolved in methanol (20 ml) and sodium hydroxide solution (0.1M, 2.0 ml) added to give a homogeneous solution. The methanol was removed under reduced pressure then the residual aqueous solution freeze dried to give the title compound (97 mg, 0.2 mmol, 100%).

$nu_{max}$(KBr) 3300, 2940, 1630, 1540, 1440, 1360, 1110, 360, and 700 cm$^{-1}$ Analysis calculated for $C_{24}H_{37}N_4O_5Na.1.5H_2O$ Requires C 56.37 H 7.88 N 10.95 Found C 56.44 H 7.40 N 10.61

$Delta_H$ (250MHz, $D_6$-DMSO) 8.26 (1H, d, J=9Hz, CON $\underline{H}$), 7.74 (1H, m, CON$\underline{H}$), 7.34–7.10 (5H, m, Aromatic H), 4.54 (1H, m, C$\underline{H}$CH$_2$Ph), 3.58 (4H, m, C$\underline{H}_2$OC$\underline{H}_2$), 3.20 (2H, m, NHC$\underline{H}_2$), 3.02–2.76 (2H, m, C$\underline{H}_2$Ph), 2.38–2.20 (10H, m, NHC$\underline{H}_2$C$\underline{H}_2$, C$\underline{H}_2$NC$\underline{H}_2$, amd C$\underline{H}$C$\underline{H}$CO), 1.38 (2H, m, CHC$\underline{H}_2$CH), 0.98–0.82 (7H, m, C$\underline{H}$(C$\underline{H}_3$)$_2$), and 0.40 (3h, d, C$\underline{H}_3$CH).

EXAMPLE 20

[4-(N-Hydroxyamino)-2R-isobutylsuccinyl]-1-phenylalanine-N-[1-(3-aminopropyl)-imidazole]amide

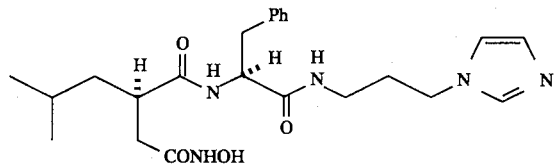

Prepared by the method described in Example 12 to give a compound with the following characteristics.

m.p. 196°–197° C.

Analysis calculated for $C_{23}H_3O_4N_5$ (0.2 mols $H_2O$) Requires C 61.30 H 7.39 N 15.68 Found C 61.36 H 7.47 N 15.81

$nu_{max}$ (KBr) 3280, 2960, 2860, 1640, 1540, 1520, 1440, 1375, 1240, 1110, 1080, 730, and 700.

$Delta_H$ (62.9MHz, $D_6$-DMSO) 0.70, (3H, d, J=6Hz), 0.76, (3H, d, J=6Hz), 1.0 (1H, m) 1.29, (2H, m), 1.76, (2H, J=7Hz), 1.92 (1H, 2d, J=8, 8Hz), 2.05 (1H, 2d, J=7, 7Hz), 2.59 (1H, m), 2.85 (1H, dd, J=9, 14Hz), 3.0 (3H, m), 3.84 (2H, t, J=7Hz), 4.39 (1H, m), 6.97, (1H, s), 7.13, (1H, s), 7.23. (5H, m), 7.58 (1H, s), 8.08 (1H, m), 8.18 (1H, d, J=8Hz), and 8.54 (1H, s).

EXAMPLE 21

[4-(N-Hydroxyamino)-2R-isobutylsuccinyl]-1-phenylalanine-N-[2-(3-aminopropyl)-pyridine]amide

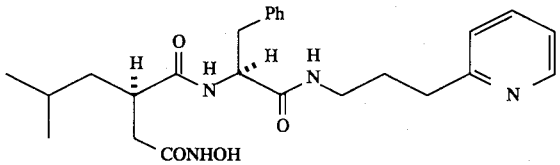

Prepared by the method described in Example 12 to give a compound with the following characteristics.

m.p. 169°–170° C.

Analysis calculated for $C_{25}H_{34}N_4O_4$ 1.3 mols $H_2O$ Requires C 62.76 H 7.11 N 11.72 Found C 63.15 H 7.32 N 11.36

$nu_{max}$ (KBr) 3280, 2950, 2920, 2860, 1660, 1535, 1435, 1000, 750, 700, and 635.

$Delta_H$ (250MHz, $D_6$-DMSO) 0.68, (3H, d, J=6Hz), 0.76 (3H, d, J=6Hz), 0.99 (1H, m), 1.34 (2H, m), 1.77, (2H, t, J=7Hz), 2.03 (2H, m), 2.65 (3H, m), 2.86 (1H, m), 3.08 (3H, m), 4.44 (1H, m), 7.20 (7H, m), 7.49 (1H, t, J=7Hz), 8.00 (1H, t, J=5Hz), 8.14 (1H, d, J=8Hz), and 8.47 (1H, d, J=4Hz).

$Delta_C$ (62.9MHz, $D_6$-DMSO) 22.0, 23.4, 25.3, 29.0, 34.8, 35.8, 37.41, 38.4, 40.6, 40.8, 54.2, 121.3, 122.9, 126.3, 128.1, 129.2, 136.5, 149.1, 161.3, 167.7, 171.0, 174.0, and 175.3.

EXAMPLE 22

[4-(N-Hydroxyamino)-2R-isobutylsuccinyl]-1-phenalanine-N-[2-aminoethyl]-N,N-diethylamine]amide

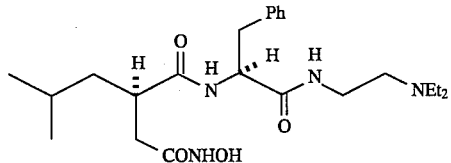

Prepared by the method described in Example 12 to give a compound with the following characteristics.

m.p. 62°–65° C.

$nu_{max}$ (KBr) 3260, 3060, 2960, 2640, 1380, 1060, 745, and 700.

$Delta_H$ (250MHz, $D_6$-DMSO) 0.76, (3H, d, J=6Hz), 0.77 (3H, d, J=6Hz), 0.96 (3H, d, J=7Hz), 1.24 (2H, m), 1.92 (1H, m), 2.14 (2H, m), 2.50 (5H, bm), 2.80 (1H, dd, J=13,10Hz), 2.99 (1H, d, J=5Hz), 3.10 (4H, bm), 3.44 (5H, bm), 4.40 (2H, m), 7.21 (5H, m), 7.78–7.91 (1H, m), and 8.12–8.37 (1H, d, J=8Hz).

$Delta_C$ (62.9MHz, $D_6$-DMSO) 11.6, 11.6, 22.0, 23.5, 25.3, 35.3, 36.7, 46.7, 51.3, 54.1, 126.2, 128.1, 129.2, 138.3, 167.3, 170.9, and 178.2.

EXAMPLE 23

[4-(N-Hydroxyamino)-2R-isobutyl-3S-methylsuccinyl]-1-phenylalanine-N-[3-aminomethyl-pyridine]amide

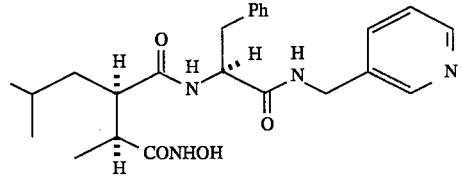

Prepared by the method described in example 11 to give a compound with the following characteristics.

m.p. 236°–238° C.

Analysis calculated for $C_{24}H_{32}N_4O_4$ (Contains 4% ash) Requires C 62.81 H 7.03 N 12.15 Found C 62.74 H 7.03 N 12.36

$nu_{max}$ (KBr) 3270, 3060, 2950, 2920, 1630, 1540, 1425, 1365, 1280, 1230, 1030, and 700.

$Delta_H$(250MHz $D_6$-DMSO) 8.53 (1H, t, J=6Hz), 8.44 (2H, dd, J=2, 5Hz), 8.34 (1H, d, J=8Hz), 7.54 (1H, dt, J=2, 8Hz), 7.31–7.14 (6H, m), 4.61 (1H, m), 4.28 (2H, t, J=5Hz), 2.97 (1H, dd, J=5, 13Hz), 2.83 (1H, dd, J=13, 11Hz), 2.50 (1H, m), 1.95 (1H, dd, J=6, 10Hz), 1.27 (3H, m), 0.84 (1H, m), 0.74 (3H, d, J=6Hz), 0.67 (3H, d, J=6Hz), and 0.42 (3H, d, J=7Hz).

$Delta_C$ (62.9MHz, $D_6$-DMSO) 172.4, 171.6, 171.5, 148.9, 148.1, 137.9, 135.01, 34.9, 129.3, 128.1, 126.3, 123.5, 54.2, 46.6, 36.4, 25.4, 21.6, and 16.1.

EXAMPLE 24

[4-(N-Hydroxyamino)-2R-isobutyl-3S-methylsuccinyl]-1-phenylalanine-N-[4-aminomethyl-pyridine]amide

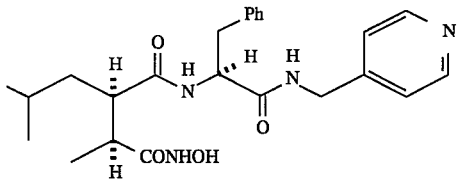

Prepared by the method described in Example 11 to give a compound with the following characteristics.

m.p. 227°–230° C.

Analysis calculated for $C_{24}H_{32}N_4O_4$-(Contains 5% ash) Requires C 62.16 H 6.95 N 12.08 Found C 62.13 H 7.06 N 11.96

$nu_{max}$ (KBr) 3300, 2960, 2935, 1640, 1605, 1560, 1440, 1370, 1030, and 700.

$Delta_H$(250MHz, $D_6$-DMSO) 0.47 (3H, d, J=7Hz), 0.69 (3H, d, J=6Hz), 0.76 (3H, d, J=6Hz), 0.83 (1H, m), 1.29 (2H, m), 1.36 (1H, m), 1.98 (1H, dd, J=7, 10Hz), 2.39 (1H, td, J=10, 3Hz), 2.84 (1H, dd, J=10, 13Hz), 2.99 (1H, dd, J=5, 14Hz), 4.27 (2H, q, J=3Hz), 4.65 (1H, m), 7.13 (2H, dd, J=2, 4Hz), 7.28 (4H, m), 8.35 (1H, d, J=8Hz), 8.44 (2H, dd, J=2, 4Hz), 8.54 (1H, t, J=6Hz), and 8.53 (H, s)

$Delta_C$ (62.9MHz, $D_6$-DMSO), 16.2, 21.6, 24.2, 25.4, 37.5, 41.2, 46.7, 54.7, 122.0, 126.4, 128.2, 129.4, 138.1, 148.4, 149.5, 171.4, 171.7, and 173.6.

EXAMPLE 25

[4-(N-Hydroxyamino)-2R-isobutyl-3S-methylsuccinyl]-1-phenylalanine-N-[2-aminomethyl-pyridine]amide

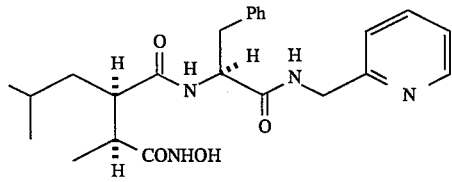

Prepared by the method described in Example 11 to give a compound with the following characteristics.

m.p. 244°–245° C.

Analysis calculated for $C_{24}H_{32}N_4O_4$ Requires C 65.43 H 7.32 N 12.72 Found C 65.18 H 7.13 N 12.60

$nu_{max}$ (KBR) 3260, 3060, 2950, 1630, 1430, 1280, 1230, 1005, 950, 745, 700, and 630.

$Delta_H$ (230MHz, $D_6$-DMSO) 0.42 (3H, d, J=7Hz), 0.68 (3H, d, J=6Hz), 0.76 (3H, d, J=6Hz), 0.84 m (1H, m), 1.30 (2H, m), 1.98 (1H, m), 2.49 (1H, m), 2.83 (1H, dd, J=11, 13Hz) 3.03 (1H, dd, J=13, 5Hz), 4.35 (2H, d, J=6Hz) 4.66 (1H, m), 7.22 (8H, m), 7.67 (1H, dd, J=2, 8Hz), 8.32 (1H, d, J=8Hz), and 8.47 (2H, m).

EXAMPLE 26

[4-(N-Hydroxyamino)-2R-isobutyl-3S-methylsuccinyl]-1-phenylalanine-N-[2-aminoethyl-pyridine]amide

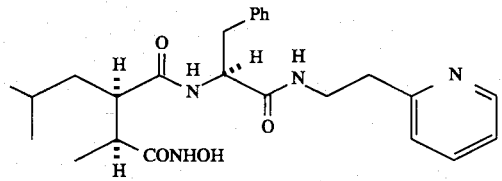

Prepared by the method described in Example 11 to give a compound with the following characteristics.

m.p. 224°–226° C.

Analysis calculated for $C_{25}H_{34}O_4N_4$ 0.4 $H_2O$ Requires C 65.04 H 7.37 N 12.15 Found C 65.01 H 7.40 N 12.04

$nu_{max}$ (KBr) 3295, 3060, 2960, 2915, 2865, 1655, 1630, 1530, 1435, 1370, 1385, 1240, 1210, 1035, 1005, 720, 690, and 635.

$Delta_H$ (250MHz, $D_6$-DMSO) 0.43 (3H, d, J=7Hz), 0.73 (3H, d, J=6Hz), 0.82 (3H, d, J=6Hz), 1.28 (2H, m), 1.94 (1H, m), 2.36 (1H, m), 2.73 (1H, m), 2.84 (3H, m), 3.37 (4H, m), 4.58 (1H, m), 7.19 (6H, m), 7.68 (1H, dt, J=2, 8Hz) 7.96 (1H, t, J=5Hz), 8.24 (1H, d, J=8Hz), and 8.52 (1H, d, J=6Hz).

$Delta_C$ (62.9MHz, $D_6$-DMSO) 16.1, 21.7, 24.2, 25.4, 37.4, 37.5, 38.5, 46.8, 54.2, 121.6, 123.2, 126.2, 128.1, 129.3, 136.6, 138.3, 149.2, 150.1, 171.3, 171.3, 171.4, and 173.4.

(e) [4-(N-Hydroxyamino)-2(RS)-isobutylsuccinyl]-L-phenylalanine-N-[4-(2-aminoethyl)-morpholine]amide

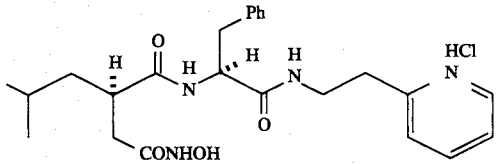

Prepared by the method described in Example 15 to give a compound with the following characteristics.

m.p. 88° C.–92° C.

Analysis calculated for $C_{24}H_{33}N_4O_4$ Cl. 3% Ash Requires C 58.61 H 6.76 N 11.39 Found C 58.41 H 6.90 N 11.42

$nu_{max}$ (KBr) 3120, 3040, 2445, 1635, 1535, 1435, 695, and 625.

$Delta_H$ (250MHz, $D_6$-DMSO) 1.02, (3H, d) 1.14 (2H, m), 1.23 (1H, m), 1.67 (2H, m), 2.42 (1H, 2d, J=15, 3Hz), 2.73 (1H, m), 2.90 (2H, m), 3.12m (1H), 3.63 (4H, m), 3.98 (2H, m), 4.10 (1H, m), 4.83 (1H, t, J=8Hz), 7.55 (1H, m, J=5Hz), 8.02 (t, 2H, J=7Hz), 8.08 (1H, s), 8.11 (1H, s), 8.38 (1H, d, J=7Hz), 8.34 (2H, m), and (1H, d, J=6Hz).

$Delta_C$ (62.9MHz, $D_6$-DMSO) 26.60, 26.71, 27.80, 28.18, 29.63, 29.93, 38.71, 39.35, 40.38, 40.80, 41.41, 43.44, 46.25, 46.90, 59.59, 59.77, 82.36, 82.88, 83.40, 128.40, 128.67, 130.91, 131.34, 131.87, 132.85, 133.73, 133.83, 142.97, 147.47, 148.52, 160.66, 161.08, 173.58, 174.07, 176.48, 176.79, and 180.01.

EXAMPLE 28

[4-(N-Hydroxyamino)-2R-isobutylsuccinyl]-1-phenylalanine-N-[4-aminomethyl-pyridine]amide hydrochloride

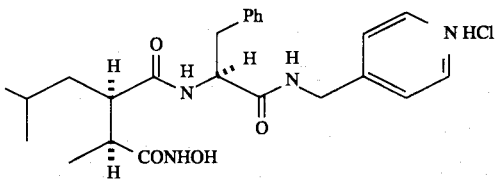

Prepared by the method described in Example 15 to give a compound with the following characteristics.

$Delta_H$(250MHz, $D_6$-DMSO) 0.47 (3H, d, J=7Hz), 0.69 (3H, d, J=6Hz), 0.76 (3H, d, J=6Hz), 0.83 (1H, m), 1.29 (2H, m), 1.36 (1H, m), 1.98 (1H, dd, J=7, 10Hz), 2.39 (1H, td, J=10, 3Hz), 2.84 (1H, dd, J=10, 13Hz), 2.99 (1H, dd, J=5, 14Hz), 4.27 (2H, q, J=3Hz), 4.65 (1H, m), 7.13 (2H, dd, J=2, 4Hz), 7.28 (4H, m), 8.35 (1H, d, J=8Hz), 8.44 (2H, dd, J=2, 4Hz), 8.54 (1H, t, J=6Hz), and 8.53 (H, s)

$Delta_C$ (62.9MHz, $D_6$-DMSO), 16.2, 21.7, 24.2, 25.4, 37.5, 41.2, 46.7, 54.7, 122.0, 126.4, 128.2, 129.4, 138.1, 148.4, 149.5, 171.4, 171.7, and 173.6

EXAMPLE 29

[4-(N-Hydroxyamino)-2R-isobutylsuccinyl]-1-phenylalanine-N-[2-aminomethyl-pyridine]amide hydrochloride

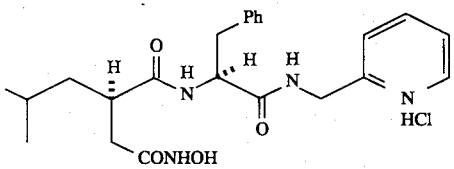

Prepared by the method described in Example 15 to give a compound with the following characteristics.

Analysis for $C_{23}H_{31}N_4O_4Cl$ Requires C 59.67 H 6.73 N 12.10 Found C 53.98 H 6.39 N 11.12

$Delta_H$ (250MHz, $CDCl_3/D_6$DMSO, 1:3) 8.46 (2H, m), 8.05 (1H, partially obscured by solvent), 7.64 (1H, dt, J=2,8 Hz), 7.22 (7H, m), 4.56 (1H, m), 4.42 (1H, s), 4.40 (1H, s), 3.17 (1H, dd, J=5,14 Hz), 2.96 (1H, dd, J=9,14 Hz), 2.67 (1H, m), 2.16 (1H, dd, J=7,14 Hz), 2.00 (1H, dd, J=14,7 Hz), 1.37 (2H, m), 1.03 (1H, m), 0.79 (3H, d, J=6Hz), and 0.75 (3H, d, J=6 Hz).

$Delta_C$ (62.9MHz, $CDCl_3/D_6$-DMSO, 1:3) 174.2, 171.2, 167.9, 158.1, 148.4, 137.9, 136.3, 129.0, 127.9, 126.0, 121.7, 120.9, 78.7, 54.3, 44.3, 40.4, 37.0, 35.7, 25.2, 23.1, and 21.8.

EXAMPLE 30

[4-(N-Hydroxyamino)-2R-isobutylsuccinyl]-1-phenylalanine-N-[2-(3-aminopropyl)-pyridine]amide hydrochloride

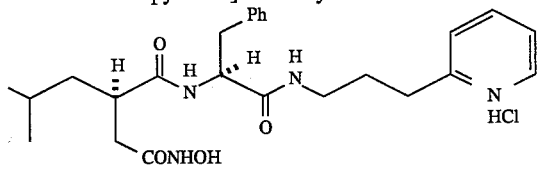

Prepared by the method described in Example 15 to give a compound with the following characteristics.

$\text{Delta}_H$ (250MHz, $D_6$-DMSO) 0.68, (3H, d, J=6Hz), 0.76, (3H, d, J=6Hz), 0.99 (1H, m), 1.34 (2H, m), 1.77, (2H, t, J=7Hz ), 2.03 (2H, m), 2.65 (3H, m), 2.86 (1H, m), 3.08 (3H, m), 4.44 (1H, m), 7.20 (7H, m), 7.86 (2H, m), 8.13 (2H, m), 8.42 (1H, t, J=7Hz), and 8.75 (1H, d, J=5Hz).

$\text{Delta}_C$ (62.9MHz, $D_6$-DMSO) 22.0, 23.4, 25.3, 29.0, 34.8, 35.8, 37.41, 38.4, 40.6, 40.8, 54.2, 121.3, 122.9, 126.3, 128.1, 129.2, 136.5, 149.1, 161.3, 167.7, 171.0, 174.0, and 175.3.

(e) [4-(N-Hydroxyamino)-2(RS)-isobutylsuccinyl]-L-phenylalanine-N-[4-(2-aminoethyl)-morpholine]amide

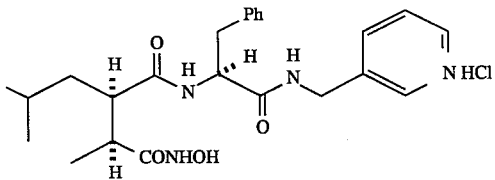

Prepared by the method described in Example 15 to give a compound with the following characteristics.

$\text{nu}_{max}$ (KBr) 3270, 3060, 2950, 2920, 1630, 1540, 1425, 1365, 1280, 1230, 1030, and 700.

$\text{Delta}_H$ (250MHz $D_6$-DMSO), 8.87 (1H, t, j=6Hz), 8.76 (2H, d, J=8Hz), 8.39 (1H, d, J=8Hz), 8.23 (1H, d, J=8Hz), 7.91 (1H, dd, J=8,6Hz), 7.31–7.14 (6H, m), 4.61 (1H, m), 4.28 (2H, t, J=5Hz), 2.97 (1H, dd, J=5, 13Hz), 2.83 (1H, dd, J=13, 11Hz), 2.50 (1H, m), 1.95 (1H, dd, J=6, 10Hz), 1.27 (3H, m), 0.84 (1H, m), 0.74 (3H, d, J=6Hz), 0.67 (3H, d, J=6Hz), and 0.42 (3H, d, J=7Hz).

$\text{Delta}_C$ (62.9MMz, $D_6$-DMSO) 172.4, 171.6, 171.5, 148.9, 148.1, 137.9, 135.0, 34.9, 129.3, 128.1, 126.3, 123.5, 54.2, 46.6, 36.4, 25.4, 21.6, and 16.1.

(e) [4-(N-Hydroxyamino)-2(RS)-isobutylsuccinyl]-L-phenylalanine-N-[4-(2-aminoethyl)-morpholine]amide

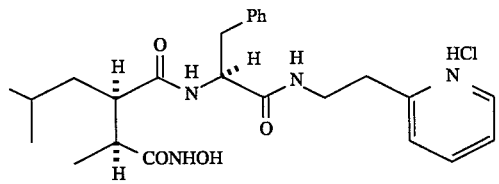

Prepared by the method described in Example 15 to give a compound with the following characteristics.

$\text{Delta}_H$ (250MHz, $D_6$-DMSO) 0.43 (3H, d, J=7Hz), 0.73 (3H, d, J=6Hz), 0.82 (3H, d, J=6Hz), 1.28 (2H, m), 1.94 (1H, m), 2.36 (1H, m), 2.67 (1H, m), 2.86 (1H, dd, J=14,4 Hz), 3.12 (2H, t, J=6Hz), 3.58 (3H,m), 4.58 (1H, m), 7.19 (6H, m), 7.83 (2H, m), 8.20 (2H, m), 8.38 (1H, t, J=7Hz), and 8.78 (1H,d, J=5Hz).

$\text{Delta}_C$ (62.9MHz, $D_6$-DMSO) 16.1, 21.7, 24.2, 25.4, 37.4, 37.5, 38.5, 46.8, 54.2, 121.6, 123.2, 126.2, 128.1, 129.3, 136.6, 138.3, 149.2, 150.1, 171.3, 171.4, and 173.4.

EXAMPLE 33

[4-(N-Hydroxyamino)-2R-isobutyl-3S-methylsuccinyl]-1-phenylalanine-N-[(2-aminomethyl)-pyridine]amide hydrochloride

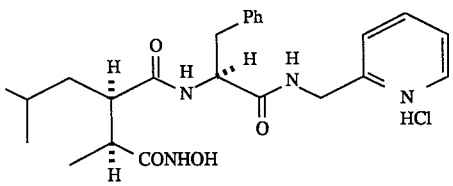

Prepared by the method described in Example 15 to give a compound with the following characteristics.

$\text{Delta}_H$ (250MHz, $D_6$-DMSO) 0.42 (3H, d, J=7Hz), 0.68 (3H, d, J=6Hz), 0.76 (3H, d, J=6Hz), 0.84 m (1H, m), 1.30 (2H, m), 1.98 (1H, m), 2.49 (1H, m), 2.83 (1H, dd, J=11, 13Hz) 3.03 (1H, dd, J=13, 5Hz), 4.35 (2H, d, J=6Hz) 4.66 (1H, m), 7.22 (8H, m), 7.48 (1h, t, J=6Hz), 7.96 (1H, dt, J=2,8Hz), 8.33 (1H, d, J=8Hz), and 8.61 (2H, t, J=6Hz).

EXAMPLE 34

[4-(N-Hydroxyamino)-2R-isobutyl-3S-methylsuccinyl]-1-phenylalanine-N-[4-aminomethyl-pyridine]amide sodium salt

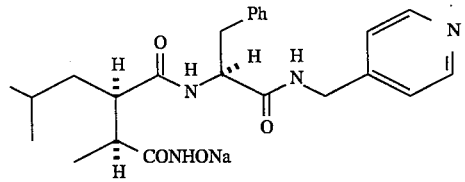

Prepared by the method described in Example 19 to give a compound with the following characteristics.

$\text{Delta}_H$(250MHz, $D_6$-DMSO) 0.47 (3H, d, J=7Hz), 0.69 (3H, d, J=6Hz), 0.76 (3H, d, J=6Hz), 0.83 (1H, m), 1.29 (2H, m), 1.36 (1H, m), 1.98 (1H, dd, J=7, 10Hz), 2.39 (1H, td, J=10, 3Hz), 2.84 (1H, dd, J=10, 13Hz), 2.99 (1H, dd, J=5, 14Hz), 4.27 (2H, q, J=3Hz), 4.65 (1H, m), 7.13 (2H, dd, J=2, 4Hz), 7.28 (4H, m), 8.35 (1H, d, J=8Hz), 8.44 (2H, dd, J=2, 4Hz), 8.54 (1H, t, J=6Hz), and 8.53 (H, s)

$\text{Delta}_C$ (62.9MHz, $D_6$-DMSO), 16.2, 21.6, 24.2, 25.4, 37.5, 41.2, 46.7, 54.7, 122.0, 126.4, 128.2, 129.4, 138.1, 148.4, 149.5, 171.4, 171.7, and 173.6.

EXAMPLE 35

4-(N-Hydroxyamino)-2R-isobutyl-3S-methylsuccinyl]-1-phenylalanine-N-[2-(2-aminoethyl)-pyridine]amide sodium salt

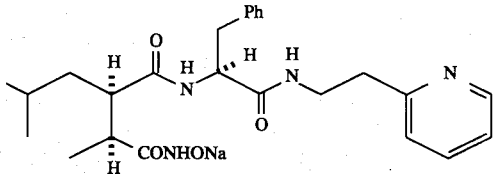

Prepared by the method described in Example 19 to give a compound with the following characteristics.

$\text{Delta}_H$ (250MHz, $D_6$-DMSO) 0.43 (3H, d, J=7Hz), 0.73 (3H, d, J=6Hz), 0.82 (3H, d, J=6Hz), 1.28 (2H, m), 1.94 (1H, m), 2.36 (1H, m), 2.73 (1H, m), 2.84 (3H, m), 3.37 (4H, m), 4.58 (1H, m), 7.19 (6H, m), 7.68 (1H, dt, J=2, 8Hz) 7.96 (1H, t, J=5Hz), 8.36 (1H, d, J=8Hz), and 8.52 (1H,d, J=6Hz).

$\text{Delta}_C$ (62.9MHz, $D_6$-DMSO) 16.1, 21.7, 24.2, 25.4, 37.4, 37.5, 38.5, 46.8, 54.2, 121.6, 123.2, 126.2, 128.1, 129.3, 136.6, 138.3, 149.2, 150.1, 171.3, 171.4, and 173.4.

EXAMPLE 36

[4-(N-Hydroxyamino)-2R-isobutyl-3S-methylsuccinyl]-1-phenylalanine-N-[3-aminomethyl-pyridine]amide sodium salt

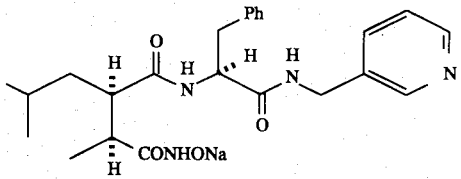

Prepared by the method described in Example 19 to give a compound with the following characteristics.

$\text{nu}_{max}$ (KBr) 3270, 3060, 2950, 2920, 1630, 1540, 1425, 1365, 7280, 1230, 1030, and 700.

$\text{Delta}_H$ (250MHz $D_6$-DMSO) 8.53 (1H, t, J=6Hz), 8.44 (2H, dd, J=2, 5Hz), 8.34 (1H, d, J=8Hz), 7.54 (1H, dt, J=2, 8Hz), 7.31–7.14 (6H, m), 4.61 (1H, m), 4.28 (2H, t, J=5Hz), 2.97 (1H, dd, J=5, 13Hz), 2.83 (1H, dd, J=13, 11Hz), 2.50 (1H, m), 1.95 (1H, dd, J=6, 10Hz), 1.27 (3H, m), 0.84 (1H, m), 0.74 (3H, d, J=6Hz), 0.67 (3H, d, J=6Hz), and 0.42 (3H, d, J=7Hz).

$\text{Delta}_C$ (62.9MHz, $D_6$-DMSO) 172.4, 171.6, 171.5, 148.9, 148.1, 137.9, 135.01, 34.9, 129.3, 128.1, 126.3, 123.5, 54.2, 46.6, 36.4, 25.4, 21.6, and 16.1.

EXAMPLE 37

[4-(N-Hydroxyamino)-2R-isobutylsuccinyl]-1-phenylalanine-N-[2-(3-aminopropyl)-pyridine]amide sodium salt

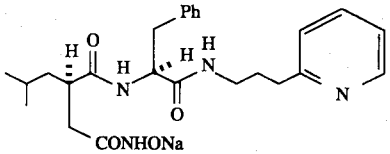

Prepared by the method described in Example 19 to give a compound with the following characteristics.

$\text{Delta}_H$ (250MHz, $D_6$-DMSO) 0.68, (3H, d, J=6Hz), 0.76 (3H, d, J=6Hz), 0.99 (1H, m), 1.34 (2H, m), 1.77, (2H, t, J=7Hz), 2.03 (2H, m), 2.65 (3H, m), 2.86 (1H, m), 3.08 (3H, m), 4.44 (1H, m), 7.20 (7H, m), 7.49 (1H, dt, J=2,7Hz), 3.14 (1H, d, J=8Hz), and 8.47 (1H, d, J=4Hz).

$\text{Delta}_C$ (62.9MHz, $D_6$-DMSO) 22.0, 23.4, 25.3, 29.0, 34.8, 35.8, 37.41, 38.4, 40.6, 40.8, 54.2, 121.3, 122.9, 126.3, 128.1, 129.2, 136.5, 149.1, 161.3, 167.7, 171.0, 174.0, and 175.3.

(e) [4-(N-Hydroxyamino)-2(RS)-isobutylsuccinyl]-L-phenylalanine-N-[4-(2-aminoethyl)-morpholine]amide

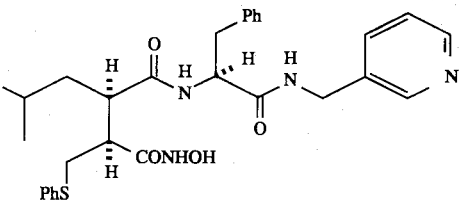

a) 2R-Bromo-5-methylpentanoic acid

D-Leucine (100 g, 0.76 mol) and potassium bromide (317.5 g, 2.67 mol) were dissolved in aqueous acid (150 ml concentrated sulphuric acid in 500 ml of water). The solution was cooled to just below 0° and sodium nitrite (69.6 g, 0.95 mol in water) was added over 1 h taking care to maintain the temperature between −1° and −2°. After addition was complete the mixture was kept at 0° for a further hour, then DCM was added and the mixture stirred for a few minutes. The layers were separated and the aqeous phase was washed with further portions of DCM (5×250 ml). The combined organic layers were dried over magnesium sulphate then the solvent removed to give the acid as a pale yellow oil (123.1 g, 0.63 mol, 83%)

[alpha]$_D$=−38.0° (c=2, methanol)

$\text{Delta}_H$ (250 MHz, CDCl$_3$) 4.29 (1H, t, J=6.5Hz, BrC$\underline{H}$CO$_2$H), 1.91 (2H, t, J=7Hz, CHC$\underline{H}_2$CH), 1.83 (1H, m, Me$_2$C$\underline{H}$), and 0.94 (6H, 2xd, J=7Hz, (C$\underline{H}_3$)$_2$CH)

a) 2R-Bromo-5-methylpentanoic acid

2R-Bromo-5-methylpentanoic acid (123 g, 0.63 mol) was dissolved in DCM (400 ml) and the solution cooled to −40° while isobutene was condensed in to roughly double the volume. Maintaining the temperature at −40° concentrated sulphuric acid (4 ml) was added dropwise. When the addition was complete the reaction was allowed to warm to room temperature overnight. The resultant solution was concentrate to half the volume by removing the solvent at reduced pressure, then the DCM was washed twice with an equal volume of 10% sodium bicarbonate solution. The organic layer was dried over magnesium sulphate and the solvent removed under reduced pressure to leave the title compound as a yellow oil (148.0 g, 0.59 mol, 94%).

[alpha]$_D$=+23.0° (c=2, methanol)

Delta$_H$ (250 MHz, CDCl$_3$) 4.18 (1H, t, J=6.5Hz, BrC$\underline{H}$CO$_2$H), 1.89 (2H, m, CHC$\underline{H}_2$CH), 1.78 (1H, m, Me$_2$C$\underline{H}$), 1.49 (9H, s, (C$\underline{H}_3$)$_3$C) and 0.94 (6H, 2xd, J=7Hz, (C$\underline{H}_3$)$_2$CH)

Delta$_C$ (63.9 MHz, CDCl$_3$) 167.0, 82.0, 46.3, 43.4, 27.6, 26.3, 22.2 and 21.6.

c) Benzyl (2-benzloxycarbonyl-3R-(tert-butoxycarbonyl)-5-methylhexanoate

Dibenzyl malonate (124.5 g, 0.44 mol) was taken up in dry DMF and potassium tert-butoxide (49.2 g, 0.44 mol) was added portionwise with stirring and cooling. When a homogeneous solution had formed it was cooled to 0° then tert-butyl-2R-bromo-5-methylpentanoate (110.0 g, 0.44 mol) in DMF (200 ml) was added dropwise over 1 h. When addition was complete the reaction was transfered to a cold room at <5° and left for 4 days. The reaction mixture was partitioned between ethyl acetate and saturated ammonium chloride then the aqueous layer extracted with further ethyl acetate (4×500 ml), drying and solvent removal left an oil (228 g) heavily contaminated with DMF. This oil was taken into ether (1 liter) and washed with brine (2×11) then the organic layer dried (magnesium sulphate), solvent removed to leave the desired material (179 g) contaminated with a small amount of dibenzyl malonate.

[alpha]$_D$=+22.5° (c=2, methanol)

Delta$_H$ (250 MHz, CDCl$_3$) 7.40–7.25 (10H, m, Aromatic H) 5.14 (4H 2xABq, C$\underline{H}_2$Ph), 3.77 (1H, d, J=13Hz, BnO$_2$CC$\underline{H}$CO$_2$Bn), 3.09 (1H, dt, J=13,6Hz, CH$_2$C$\underline{H}$CO$_2$tBu), 1.50 (3H, m, C$\underline{H}_2$+C$\underline{H}$Me$_2$)1.41 (9H, s, C(C$\underline{H}_3$)$_3$) and 0.88 (6H, 2xd, J=7Hz).

d) [4-Benzyloxy-3-benzyloxycarbonyl-2R-isobutylsuccinyl]-L-phenylalanine-N-(3-aminomethylpyridine) amide Benzyl (2-benzyloxycarbonyl-5-methyl-3R-tert-butoxycarbonyl)hexanoate (40 g) was taken up in 5% water in TFA (105 ml) and allowed to stand at 5° overnight. After this time the TFA was evaporated under reduced pressure then the residue partitioned between DCM (250 ml) and brine (50 ml). Solvent removal left an oil which crystallised on standing (30 g).

The crude acid from this reaction was dissolved in DMF (250 ml), then HOBT (13.5 g, 90 mmol), NMM (9.1 g, 90 mmol) and phenylalanine-N-(3-aminomethylpyridine) amide (23 g, 90 mmol) were added at room temperature. The mixture was cooled to 0° before dropwise addition of DCC (18.5 g, 90 mmol) in THF (250 ml). This solution was stirred to room temperature over the weekend. The precipitated DCU was removed by filtration then the solvents were removed from the filtrate under reduced pressure to leave an oil. This oily residue was dissolved in ethyl acetate then washed with 10% citric acid, 10% sodium bicarbonate and saturated brine. The organic layer was dried (magnesium sulphate), filtered then the solvent removed under reduced pressure to give the title compound as an oil (73 g). This material was columned on silica using gradient elution (0–50% ethyl acetate in hexane) to remove impurities and separate a small amount of the minor diastereoisomer. The material from the column (29.0 g, 61%) was recrystallised from ethanol/DIPE to give the title compound as a white crystalline solid (17.1 g)

e) [4-Hydroxy-2R-isobutyl-3-ethenylsuccinyl]-L-phenylalanine-N-(3-aminomethylpyridine) amide

[4-Benzyloxy-3-benzyloxycarbonyl-2R-isobutylsuccinyl] -L-phenylalanine-N-(3-aminomethylpyridine) amide (5 g, 7.9 mmol) was taken up in ethanol, ammonium formate (2.5 g, 40 mmol) added followed by 10% palladium on charcoal (1 g) as a slurry in isopropyl alcohol. After 30 minutes at room temperature the catalyst was removed by filtration, then washed with ethanol to give a solution of the crude diacid. To this was added piperidine (1 g) and the mixture stirred at room temperature for 15 minutes before addition of aqueous formaldehyde (40% solution, 5 ml). After 18 hours at room temperature the mixture was refluxed for 1 h. Solvents were removed by rotary evaporation and the residue partitioned between ethyl acetate and citric acid. The acid layer was extracted with further portions of ethyl acetate (2×250 ml), the combined organic layers were extracted with potassium carbonate (3×200 ml). These base extracts were acidified to pH 4 and re-extracted with DCM then the organic layer dried over magnesium sulphate. Solvent removal under reduced pressure gave the desired product as a white solid (2.55 g, 77%).

f) [4-Hydroxy-2R-isobutyl-3S-(phenylthiomethyl)succinyl]-L-phenylalanine-N-(3-aminomethylpyridine) amide

[4-Hydroxy-2R-isobuty-3-ethenylsuccinyl]-L-phenylalanine-N-( 3-aminomethylpyridine) amide (1 g, 2.4 mmol) was dissolved in thiophenol (10 ml) and the mixture stirred in the dark under nitrogen at 60° overnight. Ether was added to the cooled reaction mixture and the precipitated product collected by filtration. The solvent was washed with large volumes of ether and dried under vacuum to give the title compound (650 mg, 51%).

g) [4-(N-Hydroxyamino)-2R-isobutyl-3S-(phenylthiomethyl)succinyl]-L-phenylalanine-N-(3-aminomethylpyridine amide

[4-Hydroxy-2R-isobutyl-3S-phenylthiomethyl succinyl] -L-phenylalanine-N-(2-methylpyridyl) amide (0,2 g, 0.4 mmol) and HOBT (0.07 g, 0.5 mmol) were dissolved in 1:1 DCM/DMF and the mixture cooled to 0° C. before adding WSDCI (0.09 g, 0.5 mmol) and NMM (0.05 g, 0.5 mmol). The mixture was stirred at 0° C. for 1 h to ensure complete formation of the activated ester. Hydroxylamine hydrochloride (0.04 g, 0.6 mmol) and NMM (0.06 g, 0.6 mmol) were dissolved in DMF then this mixture was added dropwise to the cooled solution of the activated ester. After 1 h the reaction was poured into ether/water (1:1) whereupon the desired product precipitated as white crystals. These were collected by filtration, further washed with ether and water, then dried under vacuum at 50° C. This material was recrystallised from methanol/water (1:1) to remove a trace of the minor diastereomer (0.1 g, 0.2 mmol, 48%).

m.p. 207° C.

[alpha]$_D$=−63° (c=1, methanol)

Analysis calculated for $C_{30}H_{36}N_4O_5S$ Requires: C65.67 H6.61 N10.21 Found: C65.72 H6.71 N10.02

$delta_H$ (250MHz, $D_6$-DMSO) 8.84 (1H, s, NHO$\underline{H}$), 8.57–8.41 (3H, d CON$\underline{H}$ and aromatic H), 7.57 (1H, d, J= 6Hz, CON$\underline{H}$Me), 7.45–6.96 (7H, m, aromatic H), 4.71 (1H, m, C$\underline{H}$CH$_2$Ph), 4.30 (2H, m, C$\underline{H}_2$C$_6$H$_5$N), 2.98 (1H, dd, J=14,4Hz, CHC$\underline{H}_2$Ph), 2.82 (1H, dd, J=14,10Hz, CHC$\underline{H}_2$Ph), 2.50 (2H, m), 2.17 (2H, m), 1.33 (2H, m, C$\underline{H}$C$\underline{H}_2$(CH$_3$)$_2$), 0.85 (1H, m, C$\underline{H}_2$CH(CH$_3$)$_2$), 0.77 (3H, d, J=6Hz, CH(C$\underline{H}_3$)$_2$), and 0.70 (3H, d, J=6Hz,CH(C$\underline{H}_3$)$_2$).

EXAMPLE 39

Collagenase Inhibition Activity

The potency of compounds of general formula I to act as inhibitors of collagenase (a metalloproteas involved in tissue degradation) was determined by the procedure of Cawston and Barrett, (*Anal. Biochem.*, 99, 340–345, 1979), hereby incorporated by reference, whereby a 1 mM solution of the inhibitor being tested or dilutions thereof was incubated at 37° for 16 hours with collagen and collagenase (buffered with 25 mM Hepes, pH 7.5 containing 5 mM CaCl$_2$, 0.05% Brij 35 and 0.02% NaN$_3$). The collagen was acetylated $^{14}C$ collagen prepared by the method of Cawston and Murphy (*Methods in Enzymology*, 80, 711, 1981), hereby incorporated by reference. The samples were centrifuged to sediment undigested collagen and an aliquot of the radioactive supernatant removed for assay on a scintillation counter as a measure of hydrolysis. The collagenase activity in the presence of 1 mM inhibitor, or a dilution thereof, was compared to activity in a control devoid of inhibitor and the results reported below as that inhibitor concentration effecting 50% inhibition of the collagenase (IC$_{50}$).

| Compound of Example No. | IC$_{50}$ |
|---|---|
| 3 | 70 nM |
| 6 | 20 nM |
| 11 | 15 nM |

EXAMPLE 40

Stromelysin Inhibition Activity

The potency of compounds of general formula I to act as inhibitors of stromelysin was determined using the procedure of Cawston et al (*Biochem. J.*, 195, 159–165 1981), hereby incorporated by reference, whereby a 1 mM solution of the inhibitor being tested or dilutions thereof was incubated at 37° C. for 16 hours with stromelysin and $^{14}C$ acetylate casein (buffered with 25 mM Hepes, pH 7.5 containing 5 mM CaCl$_2$, 0.05% Brij 35 and 0.02% NaN$_3$. The casein was $^{14}C$ acetylated according to the method described in Cawston et al (*Biochem. J.*, 195, 159–165, 1981), hereby incorporated by reference. The stromelysin activity in the presence of 1 mM, or a dilution thereof, was compared to activity in a control devoid of inhibitor and the results reported below as that inhibitor concentration effecting 50% inhibition of the stromelysin (IC$_{50}$).

| Compound of Example No. | IC$_{50}$ |
|---|---|
| 11 | 50 nM |

Examples of unit dosage compositions are as follows:

EXAMPLE 41

Capsules:

| Ingredients | Per Capsule | Per 10,000 Capsules |
|---|---|---|
| 1. Active ingredient (Cpd of Formula I) | 40.0 mg | 400 g |
| 2. Lactose | 150.0 mg | 1500 g |
| 3. Magnesium stearate | 4.0 mg | 40 g |
| | 194.0 mg | 1940 g |

Procedure for Capsules:
Step 1. Blend ingredients No. 1 and No. 2 in a suitable blender.
Step 2. Pass blend from Step 1 through a No. 30 mesh (0.59 mm) screen.
Step 3. Place screened blend from Step 2 in a suitable blender with ingredient No. 3 and blend until the mixture is lubricated.
Step 4. Fill into No. 1 hard gelatin capsule shells on a capsule machine.

EXAMPLE 42

Tablets:

| Ingredients | Per Tablet | Per 10,000 Tablets |
|---|---|---|
| 1. Active ingredient (Cpd of Form. I) | 40.0 mg | 400 g |
| 2. Corn Starch | 20.0 mg | 200 g |
| 3. Alginic acid | 20.0 mg | 200 g |
| 4. Sodium alginate | 20.0 mg | 200 g |
| 5. Magnesium stearate | 1.3 mg | 13 g |
| | 101.3 mg | 1013 g |

Procedure for Tablets:
Step 1. Blend ingredients No. 1, No. 2, No. 3 and No. 4 in a suitable mixer/blender.
Step 2. Add sufficient water portionwise to the blend from Step 1 with careful mixing after each addition. Such additions of water and mixing until the mass is of a consistency to permit its conversion to wet granules.
Step 3. The wet mass is converted to granules by passing it through an oscillating granulator using a No. 8 mesh (2.38) screen.
Step 4. The wet granules are then dried in an oven at 140° F. (60° C.) until dry.
Step 5. The dry granules are lubricated with ingredient No. 5.
Step 6. The lubricated granules are compressed on a suitable tablet press.

EXAMPLE 43

Intramuscular Injection:

| Ingredient | Per ml. | Per liter |
|---|---|---|
| 1. Formula I compound Active ingredient | 10.0 mg | 10 g |
| 2. Istonic buffer solution pH 4.0. | q.s. | q.s. |

Procedure:
Step 1. Dissolve the active ingredient in the buffer solution.
Step 2. Aseptically filter the solution from Step 1.
Step 3. The sterile solution is now aseptically filled into sterile ampoules.
Step 4. The ampoules are sealed under aseptic conditions.

EXAMPLE 44

Suppositories:

| Ingredients | Per Supp. | Per 1,000 Supp |
|---|---|---|
| 1. Formula I compound Active ingredient | 40.0 mg | 40 g |
| 2. Polyethylene Glycol 1000 | 1350.0 mg | 1,350 g |
| Polyethylene Glycol 4000 | 450.0 mg | 450 g |
| | 1840.0 mg | 1,840 g |

Procedure:
Step 1. Melt ingredient No. 2 and No. 3 together and stir until uniform.
Step 2. Dissolve ingredient No. 1 in the molten mass from Step 1 and stir until uniform.
Step 3. Pour the molten mass from Step 2 into suppository moulds and chill.
Step 4. Remove the suppositories from moulds and wrap.

EXAMPLE 45

Eye Ointment

An appropriate amount of a compound of general formula I is formulated into an eye ointment base having the following composition:

| Liquid paraffin | 10% |
|---|---|
| Wool fat | 10% |
| Yellow soft paraffin | 80% |

EXAMPLE 46

Topical Skin Ointment

An appropriate amount of a compound of general formula I is formulated into a topical skin ointment base having the following composition:

| Emulsifying wax | 30% |
|---|---|
| White soft paraffin | 50% |
| Liquid paraffin | 20% |

We claim:
1. A compound of general formula IV wherein:

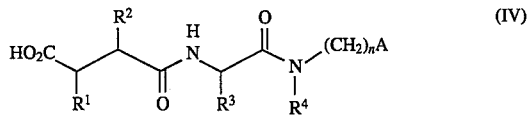

$R^1$ represents a hydrogen atom;

$R^2$ represents a $C_3$–$C_6$ alkyl, $C_2$–$C_6$ alkenyl, phenyl($C_1$–$C_6$) alkyl, cycloalkyl ($C_1$–$C_6$) alkyl, or cycloalkenyl ($C_1$–$C_6$)alkyl;

$R^3$ represents a hydrogen, para-hydroxybenzyl, hydroxymethyl, 1-hydroxyethyl, $HSCH_2$, $CH_3SCH_2CH_2$, $NH_2COCH_2$, $NH_2COCH_2CH_2$, $NH_2CH_2CH_2CH_2CH_2$, $NH_2C(NH)NHCH_2CH_2CH_2$, (COOH)$CH_2CH_2$, (COOH)$CH_2$,

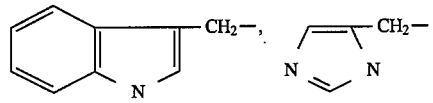

$C_1$–$C_6$ alkyl, benzyl, ($C_1$–$C_6$)alkoxybenzyl, benzyloxy($C_1$–$C_6$)alkyl or benzyloxy benzyl group;

$R^4$ represents a hydrogen atom or a methyl group;

n is an integer from 1 to 6; and

A represents the group —$NH_2$, a substituted acyclic amine of the form —N($R^A$)$R^B$, wherein one of $R^A$ and $R^B$ is a $C_1$–$C_6$ alkyl group and the other is hydrogen or a $C_1$–$C_6$ alkyl group or A represents the group pyridyl, imidazolyl, oxazolyl, thiazolyl, benzthiazolyl, benzoxazolyl, morpholinyl, pyrrolininyl or piperidinyl;

or a salt or N-oxide thereof.

2. A compound as claimed in claim 1, in which the chiral center adjacent the substituent $R^3$ has S stereochemistry.

3. A compound as claimed in claim 1, where $R^2$ represents a $C_3$–$C_6$ alkyl group.

4. A compound as claimed in claim 1, wherein $R^3$ represents a benzyl, 4-($C_1$–$C_6$)alkoxyphenylmethyl or benzyloxy benzyl group.

5. A compound as claimed in claim 1, wherein $R^4$ represents a hydrogen atom.

6. A compound as claimed in claim 1, wherein n has the value 1, 2, or 3.

7. A compound as claimed in claim 1, wherein A represents a morpholinyl, piperidinyl, 2-,3- or 4-pyridyl or pyrrolindinyl group.

8. A pharmaceutical or veterinary formulation comprising a compound as claimed in claim 1 and a pharmaceutically or veterinarily acceptable carrier.

* * * * *